US008361983B2

(12) United States Patent
Nemunaitis et al.

(10) Patent No.: US 8,361,983 B2
(45) Date of Patent: Jan. 29, 2013

(54) THERAPEUTIC RNA INTERFERENCE TECHNOLOGY TARGETED TO THE PDX-1 ONCOGENE IN PDX-1 EXPRESSING NEUROENDOCRINE TUMORS

(75) Inventors: John J. Nemunaitis, Cedar Hill, TX (US); Donald Rao, Dallas, TX (US); F. Charles Brunicardi, Houston, TX (US)

(73) Assignees: Gradalis, Inc., Carrollton, TX (US); Baylor College of Medicine, Houtson, TX (US)

( * ) Notice: Subject to any disclaimer, the term of this patent is extended or adjusted under 35 U.S.C. 154(b) by 4 days.

(21) Appl. No.: 12/913,515

(22) Filed: Oct. 27, 2010

(65) Prior Publication Data

US 2011/0117183 A1 May 19, 2011

Related U.S. Application Data

(60) Provisional application No. 61/256,867, filed on Oct. 30, 2009.

(51) Int. Cl.
*C12N 15/11* (2006.01)
*C12N 15/00* (2006.01)
*C07H 21/02* (2006.01)

(52) U.S. Cl. .................. 514/44 A; 536/24.5; 435/320.1

(58) Field of Classification Search .................. None
See application file for complete search history.

(56) References Cited

U.S. PATENT DOCUMENTS

| 5,858,973 | A | * | 1/1999 | Habener et al. ................ 514/6.9 |
| 6,716,824 | B1 | | 4/2004 | Brunicardi |
| 2002/0042388 | A1 | * | 4/2002 | Cooper et al. .................. 514/44 |
| 2003/0180950 | A1 | * | 9/2003 | Smyth Templeton ......... 435/458 |
| 2008/0269474 | A1 | * | 10/2008 | Rao .............................. 536/24.5 |
| 2009/0163431 | A1 | | 6/2009 | Kazhdan et al. |

FOREIGN PATENT DOCUMENTS

| WO | 2008101087 A1 | 8/2008 |
| WO | WO 2008/101087 A1 * | 8/2008 |

OTHER PUBLICATIONS

Zaccaro et al (Chemistry & Biology, vol. 12, 1015-1028, Sep. 2005,).*
Burgess (Acc. Chem. Res. 2001, 34, 826-835).*
Liu et al (Pancreas Aug. 2008;37:210-220).*
Okamura, Katsutomo, et al., "Distinct Roles for Qrgonaute Proteins in Small RNA-Directed RNA Cleavage Pathways," Genes and Development (2004), 18:1655-1666.
Park, John W., et al., "Anti-HER2 Immunoliposomes: Enhanced Efficacy Attributable to Targeted Delivery," Clin. Cancer Research, (2002), 8:1172-1181.
Parker, Roy, et al., "P Bodies and the Control of mRNA Translation and Degradation," Molecular Cell, Mar. 9, 2007, pp. 635-646.
Pelengaris, S., et al., "Oncogenic Co-Operation in B-Cell Tumorigenesis," Endocrine-Related Cancer, (2001), 8:307-314.
Phadke, Anagha P., et al., "Saferty and in Vivo Expressioon of a GNE-Transgene: A Novel Treatment Approach for Hereditary Inclusion Body Myopathy-2," Preclinical Studies for Gene Therapy, (2009), 3:89-101.
Pillai, Ramesh S., et al., "Tethering of Human Ago Proteins to mRNA Mimics the miRNA-Mediated Repression of Protein Synthesis," RNA, (2004), 10:1518-1525.
Pirollo, Kathleen F., et al., "Targeted Delivery of Small Interfering RNA: Approaching Effective Cancer Therapies," (2008), 68:1247-1250.
Ramesh, Rajagopal, et al., "Successful Treatment of Primary and Disseminated Human Lung Cancers by Systemic Delivery of Tumor Suppressor Genes Using an Improved Liposome Vector," Mar. 2001, Molecular Therapy, vol. 3, No. 3, pp. 337-350.
Sakai, H., et al., "PDX1 Homeobox Protein Expression in Pseudopyloric Glands and Gastric Carcinomas," Gut, (2004), pp. 323-330.
Scherr, Michaela, et al., "Specific Inhibition of bcr-abi Gene Expression by Small Interfering RNA," Blood, Sep. 26, 2002, 14 pages.
Senzer, Neil, et al., "Letter to the Editor: Does Dicer Expression Affect shRNA Processing," Gene Regulation and Systems Biology, (2009), 3:103-104.
Serup, Palle, et al., "Induction of Insulin and Islet Amyloid Polypeptide Production in Pancreatic Islet Glucagonoma Cells by Insulin Promoter Factor 1," Proc. Natl. Acad. Sci., Aug. 1996, vol. 93, pp. 9015-9020.
Silva, Jose M., et al., "Second-Generation shRNA Libraries Covering the Mouse and Human Genomes," Nature Genetics, Nov. 2005, vol. 7, No. 11, pp. 1281-1288.
Simoes, S., et al., "Mechanisms of Gene Transfer Mediated by Lipoplexes Associated with Targeting Ligands or pH-Sensitive Peptides," Gene Therapy, (1999), 6:1798-1807.
Singh, Anju, et al., "RNAi-Mediated Silencing of Nuclear Factor Erythroid-2-Related Factor 2 Gene Expression in Non-Small Cell Lung Cancer Inhibits Tumor Growth and Increases Efficacy of Chemotherapy," Cancer Res., (2008), 68 (19):7975-7984.
Takei, Yoshifumi, et al., "A Small Interfering RNA Targeting Vascular Endothelial Growth Factor as Cancer Therapeutics," Cancer Research, May 15, 2004, 64:3365-3370.
Tomari, Yukihide, et al., "Sorting of Drosophila Small Silencing RNAs," Cell, Jul. 27, 2007, 130(2):299-308.
Tong, Alex W., et al., "Systemic Therapeutic Gene Delivery for Cancer: Crafting Paris' Arrow," Current Gene Therapy, (2009), 9:45-60.
Uchida, Hiroaki, et al., "Adenovirus-Mediated Transfer of siRNA Against Survivin Induced Apoptosis and Attenuated Tumor Cell Growth in Vitro and in Vivo," Molecular Therapy, Jul. 2004, vol. 10, No. 1, pp. 162-171.
Valencia-Sanchez, Marco, et al., "Control of Translation and mRNA Degradation by miRNAs and siRNAs," Genes & Development, (2006), 20:515-524.

(Continued)

*Primary Examiner* — Richard Schnizer
(74) *Attorney, Agent, or Firm* — Edwin S. Flores; Chalker Flores, LLP

(57) ABSTRACT

A bifunctional shRNA-based composition and methods for knocking down the expression of the PDX-1 oncogene in target cells is described herein. The invention also provides methods to deliver the shRNA-containing expression vectors to target tissues overexpressing the PDX-1 oncogene.

34 Claims, 11 Drawing Sheets

OTHER PUBLICATIONS

Verma, Udit N., et al., "Small Interfering RNAs Directed Against Beta Catenin Inhibit the in Vitro and in Vivo Growth of Colon Cancer Cells," Clin. Cancer Res., (2003), 9:1291-1300.

Wyszko, Eliza, et al., "A Multivariate Analysis of Patients with Brain Tumors Treated with ATN-RNA," Acta Poloniae Pharmaceutica, (2008), vol. 65, No. 6, pp. 677-684.

Yague, E., et al., "Complete Reversal of Multidrug Resistance by Stable Expression of Small Interfering RNAs Targeting MDR1," Gene Therapy, (2004), 11:1170-1174.

Yang, Gong, et al., "Inhibition of Breast and Ovarian Tumor Growth through Multiple Signaling Pathways by Using Retrovirus-Mediated Small Interfering RNA Against Her-2/neu Gene Expression," The Journal of Biological Chemistry, Feb. 6, 2004, vol. 279, No. 6, pp. 4339-4345.

Yoshinouchi, Mitsuo, et al., "In Vitro and in Vivo Growth Suppression of Human Papillomavirus 16-Positive Cervical Cancer Cells by E6 siRNA," Molecular Therapy, Nov. 2003, vol. 8, No. 5, pp. 762-768.

Yuan, Fan, et al., "Vascular Permeability and Microcirculation of Gliomas and Mammary Carcinomas Transplanted in Rat and Mouse Cranial Windows," Cancer Research, (1994), 54:4564-4568.

Yurek, David M., et al., "Long-Term Transgene Expression in the Central Nervous System Using DNA Nanoparticles," Molecular Therapy, Apr. 2009, vol. 17, No. 4, pp. 641-650.

Yurek, David M., et al., "Compacted DNA Nanoparticle Gene Transfer of GDNF to the Rat Striatum Enhances the Survival of Grafterd Fetal Dopamine Neurons," Cell Transplant, (2009), 18(10:1183-1196.

Zaccaro, Maria Ciara, et al., "Selective Small Molecule Peptidomimetic Ligands of TrkC and TrkA Receptors Afford Discrete or Complete Neurotrophic Activities," Chemistry & Biology, (Sep. 2005, vol. 12, pp. 1015-1028.

Zeng, Yan, et al., "Sequence Requirements for Micro RNA Processing and Function in Human Cells," RNA, (2003), 9:112-123.

Ziady, Assem-Galal, et al., "Transfection of Airway Epithelium by Stable PEGylated Poly-L-Lysine DNA Nanoparticles in Vivo," Molecular Therapy, Dec. 2003, vol. 8, No. 6, pp. 936-947.

Ziady, Assem-Galal, et al., "Minimal Toxicity of Stabilized Compacted DNA Nanoparticles in the Murine Lung," Molecular Therapy, Dec. 2003, vol. 8, No. 6, pp. 948-956.

Zukiel, Ryszard, et al., "Suppression of Human Brain Tumor with Interference RNA Specific for Tenascin-C," Cancer Biology & Therapy, Aug. 2006, 5:8, pp. 1002-1007.

Aharinejad, Seyedhossein, et al., "Colony-Stimulating Factor-1 Blockade by Antisense Oligonucleotides and Interfering RNAs Suppresses Growth of Human Mammary Tumor Senografts in Mice," Cancer Research, (Aug. 1, 2004, vol. 64, pp. 5378-5384.

Bartlett, Derek W., "Impact of Tumor-Specific Targeting on the Biodistribution and Efficacy of siRNA Nanoparticles Measured by Multimodality in vivo Imaging," PNAS, Sep. 25, 2007, vol. 104, No. 39, pp. 15549-15554.

Blaszkowsky, Lawrence, "Treatment of Advanced and Metastatic Pancreatic Cancer," Frontiers in Bioscience, Nov. 1, 1998, pp. e214-e225.

Bretherton-Watt, Deborah, et al., "Insulin Upstream Factor 1 and a Novel Ubiquitous Factor Bind to the Human Islet Amyloid Polypeptide/Amylin Gene Promoter," Biochem. J., (1996), vol. 313, pp. 495-502.

Brummelkamp, Thijn R., et al., "Stable Suppression of Tumorigenicity by Virus-Mediated RNA Interference," Cancer Cell, Aug. 22, 2002, 5 pages.

Bruno, Martin A., et al. "Long-Lasting Rescue of Age-Associated Deficits in Cognition and the CNS Cholinrgic Phenotype by a partial Agonist Peptidomimetic Ligand of TrkA," The Journal of Neuroscience, Sep. 15, 2004, vol. 24, pp. 8009-8018.

Cai, Xue, et al., "A Partial Structural and Functional Rescue fo a Retinitis Pigmentosa Model with Companced DNA Nanoparticles," PLOS One, Apr. 2009, vol. 4, Issue 4, 11 pages.

Calvo, A., et al., "identification of VEG-regulated Genes Associated with Increased Lung Metastic Potential: Functional Involvement of Tenasic-C in Tumor Growth and Lung Metastasis," Oncogene, Sep. 11, 2008, 27 (40:5373-5384.

Chen, Caifu, et al., "Real-Time Quantification of MicroRNAs by Stem-Loop RT-PCR," Nucleic Acides Research, 2005, vol. 33, No. 208, 9 pages.

Chen, Xugang, et al., "Cell Surface Nucleolin Serves as Receptor for DNA Nanoparticles Composed of Pegylated Polylysine and DNA," Molecular Therapy, vol. 15, No. 2, pp. 333-342, 2008.

Choudhury, et al., "Small Interfering RNA (SiRNA)Inhibits the Expression of the Her2/Neu Gene, Upregulated HLA Class I and Invoices Apoptosis of Her2/Neu Positive Tumor Cell Lines," Int. J. Cancer., (108, vol. 108, pp. 71-77, 2004).

Cioca, Daniel P., et al., "RNA Interference is a Functional Pathway with Therapeutic Potential in Human Myeloid Leukemia Cell Lines," Cancer Gene Therapy, (2003), vol. 10, pp. 125-133.

Cullen, Bryan R., "RNAi the Natural Way," Nature Genetics,(Nov. 2005, vol. 37, No. 11, pp. 1163-1165.

Ding, Xi-Qin, et al., "Ocular Delivery of Compacted DNA-Nanoparticles Does Not Elicit Toxicity in the Mouse Retina," PLOS ONE, Oct. 2009, vol. 4, Issue 10, pp. 11 pages.

Duxbury, Mark S., et al., "Systemic siRNA-Mediated Gene Silencing a New Approach to Targeted Therapy of Cancer," Annals. of Surgery, Oct. 2004, vol. 240, No. 4, pp. 667-676.

Farjo, Rafal, et al., "Efficient Non-Viral Ocular Gene Transfer with Compacted DNA Nanoparticles," PLOS ONE, Dec. 2006, Issue 1, 8 pages.

Filleur, Stephanie, et al., "SiRNA-Mediated Inhibition of Vascular Endothelial Growth Factor Severely Limits Tumor Rsistance to Antiangiogenic Thrombospondin-1 and Slows Tumor Vascularization and Growth," Cancer Res., (2003), vol. 63, pp. 3919-3922.

Fink, TL, et al., "Plasmid Size up to 20 KBP Does Not Limit Effective in Vivo Lung Gene Transfer Using Compacted DNA Nanoparticles," Gene Therapy, (2006), vol. 13, pp. 1048-1051.

Forstemann, Klaus, et al., "Drosophila MicroRNAs are Sorted into Functionally Distinct Argonaute Protein Complexes after their Production by Dicer-1," Cell, Jul. 27, 2007, 130(2):287-297.

Frank, Oliver, et al., "Tumor Cells Escape Suicide Gene Therapy by Genetic and Epigenetic Instability," (2004), 104:3543-3549.

Hagman, Derek K., et al., "Palmitate Inhibits Insulin Gene Expression by Altering PDX-1 Nuclear Localization and Reducing MafA Expression in Isolated Rat Islets of Langerhans," The Journal of Biological Chemistry, Sep. 16, 2005, vol. 280, No. 37, pp. 32413-32418.

Hashizume, Hiroya, et al., "Openings between Defective Endothelial Cells Explain Tumor Vessel Leakiness," American Journal of Pathology, Apr. 2000, vol. 156, No. 4, pp. 1363-1380.

Heidel, Jeremy D., et al., "Potent siRNA Inhibitors of Ribonucleotide Reductase Subunit RRM2 Reduce Cell Proliferation in vitro and in vivo," Clin. Cancer Res., (2007), 13:2207-2215.

Heidel, Jeremy D., et al., "Administration in Non-Human Primates of Escalating Intravenous Doses of Targeted Nanoparticles Containing Ribonucleotide Reductase Subunit M2 siRNA," Apr. 3, 2007, vol. 104, No. 14, pp. 5715-5721.

Hirshberg, Boaz, et al., "Malignant Insulinoma," Cancer, Jul. 15, 2005, vol. 104, No. 2, pp. 264-272.

Hutvagner, Gyorgy, et al., "A MicroRNA in a Multiple-Turnover RNAi Enzyme Complex," Science Express, Aug. 1, 2002, 8 pages.

Iancu, Camelia, et al., Effects of Stathmin Inhibition on the Mitotic Spindle,: Journal of Cell Science, vol. 114, pp. 909-916, 2001.

International Search Report and Written Opinion for PCT/US2010/054350, dated Aug. 10, 2011, 12 pages.

Ito, Isao,e t al., "Liposomal Vector Mediated Delivery of the 3p FUS1 Gene Demonstrates Potent Antitumor Activity Against Human Lung Cancer in vivo," Cancer Gene Therapy, (2004), vol. 11, pp. 733-739.

Jay, Chris, et al., "Preclinical Assessment of wt GNE Gene Plasmid for Management of Hereditary Inclusion Body Myopathy 2 (HIBM2)," Gene Regulation and Systems Biology, (2008), 2:243-252.

Judge, Adam D., et al., "Confirming the RNAi-Mediated Mechanism of Action of siRNA-Based Cancer Therapeutics in Mice," The Journal of Clinical Investigation, Mar. 2009, vol. 119, No. 3, pp. 661-673.

Kaltsas, Gregory A., et al., "The Diagnosis and Medical Management of Advanced Neuroendocrine Tumors," Endocrine Reviews, Jun. 2004, 25(3):458-511.

Kawasaki, Hiroaki, al., "Short Hairpin Type of dsRNAs that are Controlled by tRNA VAL Promoter Significantly Induce RNAi-Mediated Gene Silcencing in the Cytoplasm of Human Cells," Nucleic Acids Research, (2003), vol. 31, No. 2, pp. 700-707.

Khalil, Ikramy A., et al., "Uptake Pathways and Subsequent Intracellular Trafficking in Nonviral Gene Delivery," Pharmacological Reviews, (2006), 58(1):32-45.

Kirpotin, Dmitri B., et al., "Antibody Targeting of Long-Circulating Lipidic Nanoparticles Does Not Increase Tumor Localization but Does Increase Internalization in Animal Models," Cancer Research, (2006), 66:6732-6740.

Konstan, Michael W., et al., "Compacted DNA Nanoparticles Administrered to the Nasal Mucosa of Cystic Fibrosis Subjects are Safe and Demonstrate partial to Complete Cystic Fibrosis Transmembrane Regulator Reconstitution," Human Gene Therapy, Dec. 2004, 15:1-15.

Kosciolek, Barbara A., et al., "Inhibition of Telomerase Activity in Human Cancer Cells by RNA Interference," Mol. Cancer Ther., (2003), 2:209-216.

Lakka, Sanjani S., et al., "Inhibition of Cathepsin B and MMP-9 Gene Expression in Glioblastoma Cell Line via RNA Interference Reduces Tumor Cell Invasion, Tumor Growth and Angiogenesis," Oncogene, (2004), 23:4681-4689.

Landthaler, Markus, et al., "Molecular Characterization of Human Argonaute-Containing Ribonucleoprotein Complexes ad their Bound Target mRNAs," RNA, (2008), 14:2580-2596.

Li Kaiyi, et al., "Use of RNA Interference to Target Cyclin E-Overexpressing Hepatocellular Carcinoma," Cancer Research, (2003), 63:3593-3597.

Li, Shyh-Dar, et al., "Tumor-Targeted Delivery of siRNA by Self-Assembled Nanoparticles," Molecular Therapy, Jan. 2008, 16(1):163-169.

Liu, Ge, et al., "Nanoparticles of Compacted DNA Transfect Postmitotic Cells," The Journal of Biological Chemistry, (2003), vol. 278, No. 35, pp. 32578-32586.

Liu, Shi-He, et al., "PDX-1 Demonstration of Oncogenic Properties in Pancreatic Cancer," Cancer, (2010), 11 pages.

Liu, Shihe, et al., "PDX-1 Acrts as a Potential Molecular Target for Treatment of Human Pancreatic Cancer," Pancreas, (2008), 37:210-220.

Maeda, Noriyuki, et al., "Enhancement of Anticancer Activity in Antineovascular Therapy is Based on the Intratumoral Distribution of the Active Targeting Carrier for Anticancer Drugs," Biol. Pharm. Bull., (2006), 29(9):1936-1940.

Martinez, Luis Aflonso, et al., "Synthetic Small Ibhibiting RNAs: Efficient Tools to Inactivate Oncogenic Mutations and Restore p53 Pathways," PNAS, Nov. 12, 2002, vol. 99, No. 23, pp. 14849-14854.

Merritt, William M., et al., "Dicer, Drosha, and Outcomes in Patients with Ovarian Cancer," New England Journal of Medicine, (Dec. 18, 1008), 359:2641-2650.

Miyatsuka, Takeshi, et al., "Persistent Expression of PDX-1 in the Pancreas Causes Acinar-to-Ductal Metaplasia through Stat3 Activation," Genes Dev., (2006), vol. 20, pp. 1435-1440.

Miyoshi, Keita, et al., "Slicer Function of Drosophila Argonautes and its Involvement in RISC Formation," Genes & Development, (2005), 19:2837-23848.

Nakahira, Shin, et al., "Involvement of Ribonucleotide Reductase M1 Submit Overexpression in Gemcitabine Resistance of Human Pancreatic Cancer," (2007), Int. J. Cancer. 120:1355-1363.

\* cited by examiner

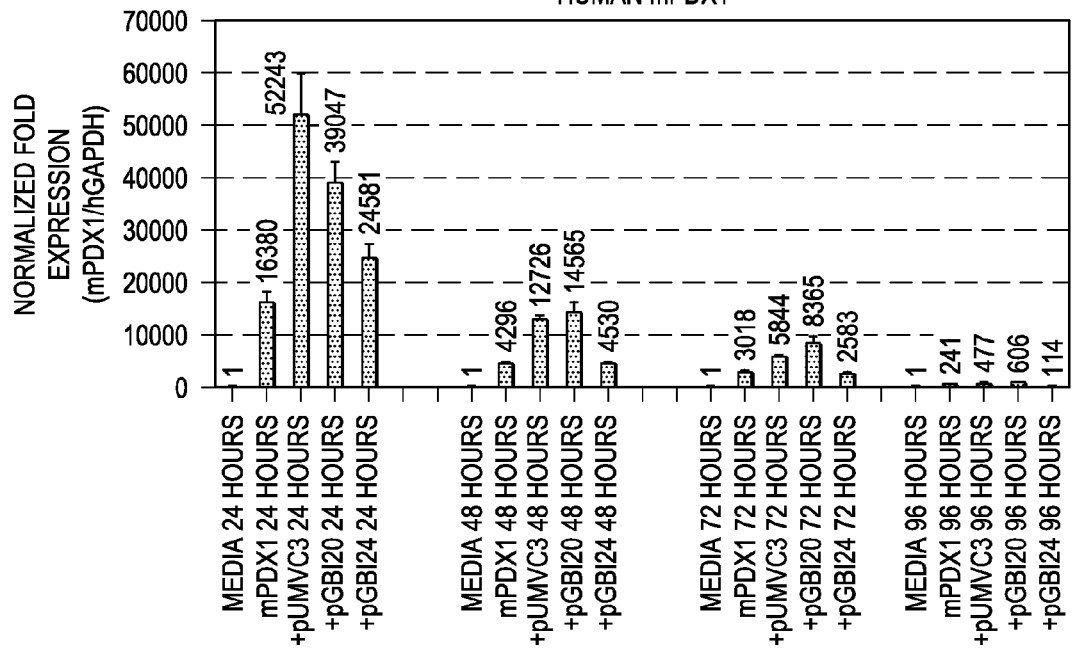
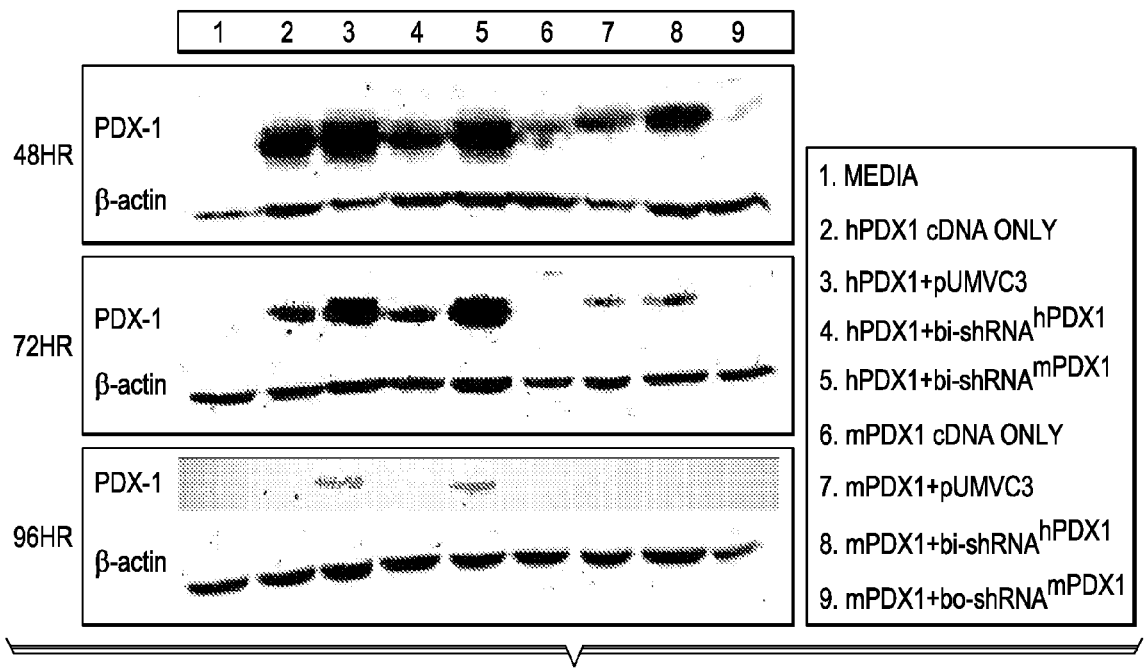
FIG. 4

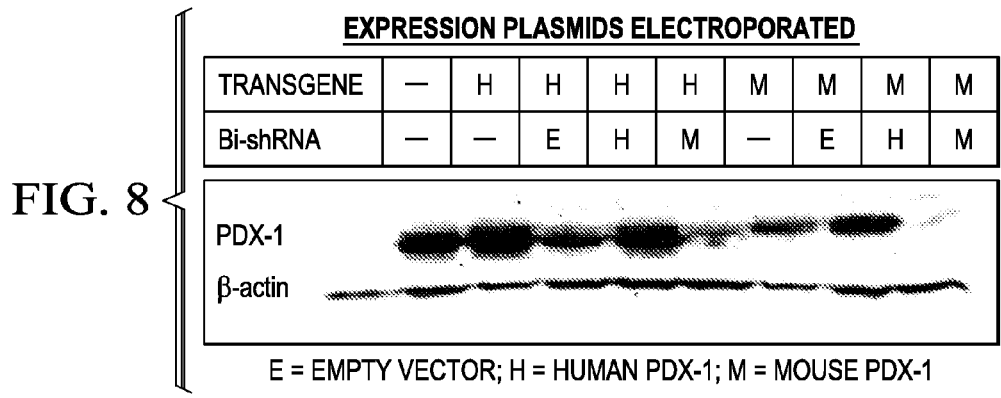
FIG. 8
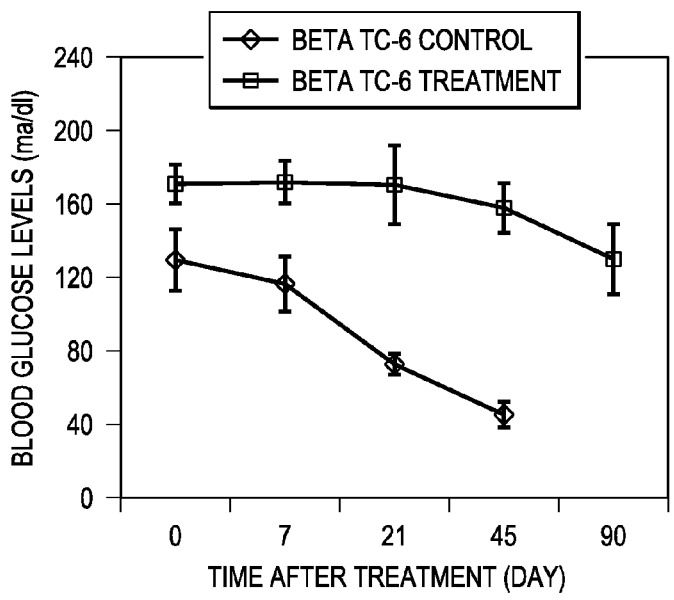
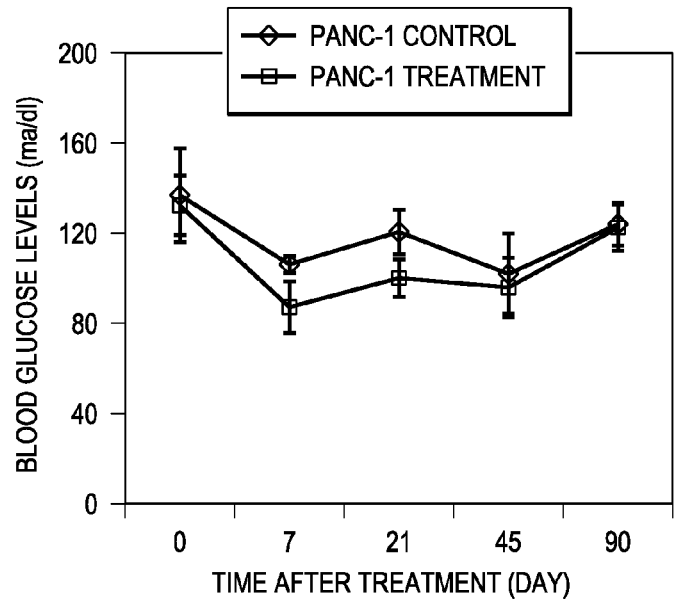

THERAPEUTIC RNA INTERFERENCE TECHNOLOGY TARGETED TO THE PDX-1 ONCOGENE IN PDX-1 EXPRESSING NEUROENDOCRINE TUMORS

CROSS-REFERENCE TO RELATED APPLICATIONS

This application claims priority to U.S. Provisional Application Ser. No. 61/256,867, filed Oct. 30, 2009, the entire contents of which is incorporated herein by reference.

TECHNICAL FIELD OF THE INVENTION

The present invention relates in general to the field of gene-targeted cancer therapy, and more particularly, to the development of novel therapies and drug delivery systems for the treatment of pancreatic neuroendocrine tumors.

STATEMENT OF FEDERALLY FUNDED RESEARCH

None.

REFERENCE TO A SEQUENCE LISTING

The present application includes a Sequence Listing filed separately in an electronic format as required by 37 C.F.R §1.821-1.825.

BACKGROUND OF THE INVENTION

Without limiting the scope of the invention, its background is described in connection with the design and delivery of shRNA-based therapies targeting the expression of the PDX-1 oncogene as treatments for pancreatic neuroendocrine tumors.

Islet neoplasia refers collectively to disorders emanating from pancreatic islet cells, such as pancreatic neuroendocrine tumors (NET), insulinomas, and carcinoid. Islet cell tumors have a 5-year survival rate between 35-50% [1, 2]. Islet neoplasia affects relatively young patients (age at diagnosis 50 years) [3, 4]. Patients with insulinoma in particular suffer horribly from uncontrollable hypoglycemia, for which there is no effective treatment. Hypoglycemia results from hyperinsulinemia and manifests with symptoms of neuroglycopenia, such as headache, dizziness, lethargy, diplopia, seizures and sympathetic activation [3]. Surgery remains the most effective treatment modality, and there are no effective adjuvant therapies. When synchronous resection of the primary tumor and metastases is possible, recurrence rates remain high. Moreover, survival has not improved with systemic therapy [5, 6]. Thus, a need exists for novel and effective therapeutic approaches to treat NET.

Pancreatic duodenal homeobox-1 (PDX-1) is an embryonic transcription factor of pancreatic organogenesis that is over expressed in most NET's and all islet cell insulinomas. The transcription factor PDX-1 gene is directly responsible for regulating insulin secretion in benign and malignant insulinomas [7-10]. It is also found in a variety of cancers where it appears to be associated with proliferation, differentiation, and migration, with a primary role in the development of NET and pancreatic embryogenesis [7-14]. In the adult pancreas, PDX-1 is expressed by 90% of β cells, where it has been shown to regulate expression of insulin, glucokinase, and glucose transporter type 2 (GLUT2) [15-19]. These genes have a critical role in maintaining glucose homeostasis in both acute and chronic hyperglycemia. In acute hyperglycemia, PDX-1 migrates from the cytoplasm to the nucleus of β-cells and activates the insulin gene, the first step in increased insulin production and secretion [20, 21].

PDX-1 was shown to be overexpressed in a number of cancers by the present inventors and others [22-25]. In particular, the present inventors found that PDX-1 was overexpressed in more than 80 pancreatic cancers and islet cell neoplasias [26]. One hundred percent of insulinomas also have PDX-1 overexpression. The inventors have recently demonstrated that PDX-1 regulates proliferation and invasion of pancreatic cancer and insulinoma cell lines [27]. It will be appreciated by those skilled in the art that if the compositions and methods to modulate the overexpression of PDX-1 in cancers are provided, such compositions and methods would have a positive value and represent a substantial contribution to the art. Likewise, it will be appreciated by those versed in the drug delivery art that if a delivery system is provided to bypass non-target organs and target the delivery of the therapeutic agent to the target organs over expressing PDX-1, such a delivery system would be clinically useful in the practice of medicine. A strategy for treating pancreatic adenocarcinoma by targeting PDX-1 is provided in U.S. Pat. No. 6,716,824 issued to Brunicardi (2004) that relates to a recombinant nucleic acid for an RIP-tk (rat insulin promoter-thymidine kinase) construct that selectively targets insulin secreting cells, such as β-cells, PDX-1 positive human pancreatic ductal carcinomas, and other cells containing certain transcription factors. The Brunicardi invention is useful in the treatment of pancreatic cancers, such as β-cell insulinomas.

Preclinical studies confirm that RNA interference techniques (RNAi) can be used to silence cancer-related targets [28-38]. In vivo studies have also shown favorable outcomes by RNAi targeting of components critical for tumor cell growth [29, 39-42], metastasis [43-45], angiogenesis [46, 47], and chemoresistance [48-50]. Applications of the RNAi technology initially employed two types of molecules; the chemically synthesized double-stranded small interfering RNA (siRNA) or vector based short hairpin RNA (shRNA). Although siRNA and shRNA can achieve similar knockdown functions, siRNA and shRNA are intrinsically different molecules. shRNAs, which share the same biogenesis pathways as the naturally occurring microRNAs (miRNAs), are processed and transported to the cytoplasm where they load onto the RNA interference silencing complexes (RISC) [51]. The primary transcripts of endogenous miRNAs are synthesized from genomic DNA in the nucleus as long RNA strands with hairpin structures, which are processed to mature 21-23 base pair double stranded miRNA by a series of endogenous RNase III enzymes. At least two RNase III enzyme complexes are involved in the maturational process; first, the Drosha/DGCR8 complex produces the pre-miRNA hairpin structure which, following nuclear export, is incorporated into the RLC where the second enzyme, Dicer, excises the loop producing the mature miRNA [52], the effector molecule that is loaded onto RISC for RNAi [53].

The Argonaute (Ago) family of proteins commonly associates with the cytoplasmic RISC. These proteins are involved in the loading of siRNA or miRNA, and are also implicated in both transcriptional (targeting heterochromatin) and post-transcriptional gene silencing. The guide strand of siRNA or miRNA loaded onto Ago-complexed RISCs seeks out target mRNAs with sequence complementarity. Endonucleolytically active Ago-2 cleaves mRNA to initiate mRNA degradation [54, 55]. Alternatively, partial complementary binding to the 3' UTR of the targeted mRNA achieves translational repression through sequestration in processing bodies (P-bodies) [56]. Deadenylation leading to destabilization of the target mRNA has been observed in P-bodies [57, 58]. There is now compelling evidence in numerous animal models that RNAi-mediated gene knockdown is potent, specific, and well tolerated. These findings provide the scientific rationale for the translation of RNAi therapeutics into the clinic. At least 10 RNAi-based drugs are now in early phase clinical trials [59], four of which are cancer related [60-63]. Additional siRNAs have also demonstrated efficacy in animal models [60, 61, 64] and safety in non-human primates [65].

U.S. Patent Application No. 2009/0163431 (Kazhdan et al., 2009) discloses methods and compositions for inhibiting PDX-1. An anti-PDX-1 agent included in inventive methods and compositions that includes an antibody, an aptamer, an antisense oligonucleotide, a ribozyme and/or an inhibitory compound. Methods of inhibiting PDX-1 expression in a tumor cell are provided by the present invention which include contacting a tumor cell with an effective amount of an anti-PDX-1 agent highly or completely complementary to a specified region of an RNA molecule encoding PDX-1. Such an agent specifically hybridizes with the RNA molecule encoding PDX-1 and inhibits the expression of a PDX-1 gene in the tumor cell. Compositions including anti-PDX-1 siRNA and/or shRNA are described. Recombinant expression constructs encoding anti-PDX-1 siRNA or shRNA according to the present invention are described.

SUMMARY OF THE INVENTION

The present invention includes a PDX bi-shRNA, for concurrently inducing translational repression and post-transcriptional mRNA degradation of its target. The PDX bi-shRNA construct achieves higher efficacy and prolonged activity as compared to siRNAs with the same mRNA target specificity. The inventors have shown that PDX-1 knockdown induces apoptosis, arrests proliferation, and reduces invasiveness of NET cancer cells, and improves survival of SCID mice bearing carcinoma xenografts. The inventors have also demonstrated that multiple treatments of IV (intravenous) BIV liposomal PDX-1 shRNA resulted in near complete ablation of human PC xenografts in SCID mice and have confirmed response and survival advantage in a murine insulinoma model.

Bilamellar invaginated vesicles (BIV) are a delivery system in which temporarily masked, targeted liposomes are used to deliver therapeutics into cells by fusion with the cells membrane. These masked stealthed liposomes achieve higher transfection efficiencies by avoiding the endocytotic pathway. The Copernicus compacted nucleic acid delivery technology is another non-viral synthetic and modular platform in which single molecules or DNA or RNA are compacted by polycations to yield nanoparticles with very high transfection efficiencies. The inventors have developed a novel cancer therapy approach by packaging of compacted shRNA-containing DNA nanoparticles in masked stealthed BIV liposomes.

The present invention includes an expression vector comprising a promoter and a nucleic acid insert operably linked to the promoter, wherein the insert encodes one or more short hairpin RNAs (shRNA) capable of hybridizing to a region of a transcript encoding the PDX-1 transcription factor. The binding of the shRNA to the transcript inhibits PDX-1 expression via RNA interference. The shRNA may be bifunctional, incorporating both siRNA (cleavage-dependent) and miRNA (cleavage-independent) motifs simultaneously. In one embodiment of the present invention, the shRNA is both the cleavage-dependent and cleavage-independent inhibitor of PDX-1 expression. The mRNA sequences targeted by the shRNA are not limited to the 3' untranslated (UTR) region of the PDX-1 mRNA transcript; in one embodiment of the present invention, the shRNA may target coding sequences. In one aspect the one or more shRNA comprise a sequence selected from the group consisting of SEQ. ID NO: 3, SEQ. ID NO: 4, SEQ. ID NO: 5, SEQ. ID NO: 6, SEQ. ID NO: 7, SEQ. ID NO: 8, and combinations or modifications thereof.

The present invention also provides a system to deliver the shRNAs to the PDX-1 mRNA target. The delivery system comprises a therapeutic agent carrier, such as a liposome, coupled to an expression vector comprising a promoter and a nucleic acid insert operably linked to the promoter, wherein the insert encodes one or more short hairpin RNAs (shRNA) capable of hybridizing to a region of a transcript encoding the PDX-1 transcription factor. The one or more shRNA comprise a sequence selected from the group consisting of SEQ. ID NO: 3, SEQ. ID NO: 4, SEQ. ID NO: 5, SEQ. ID NO: 6, SEQ. ID NO: 7, SEQ. ID NO: 8, and combinations or modifications thereof. The binding of the shRNA to the transcript inhibits PDX-1 expression via RNA interference. The shRNA may be bifunctional, incorporating both siRNA (cleavage-dependent) and miRNA (cleavage-independent) motifs. In one embodiment of the present invention, the shRNA is both the cleavage-dependent and cleavage-independent inhibitor of PDX-1 expression. The mRNA sequences targeted by the shRNA are not limited to the 3' untranslated (UTR) region of the PDX-1 mRNA transcript; in one embodiment of the present invention, the shRNA may target coding sequences. The therapeutic agent carrier may be a compacted DNA nanoparticle. In one embodiment, the DNA of the expression vector may be compacted by combining it with polycations. More particularly, the DNA may be compacted by combining it with $CK_{30}PEG10k$, a 10 kD polyethylene glycol (PEG) modified with a peptide comprising a N-terminus cysteine and 30 lysine residues. The therapeutic agent carrier may also be a liposome in which the DNA may be compacted by combining it with a 30 mer lysine condensing peptide. In one embodiment, the liposome may be a bilamellar invaginated vesicle (BIV). The liposome may be specifically targeted to a target tissue by decorating it with "smart" receptor targeting moieties. In one example, the targeting moieties may be small molecule bivalent beta-turn mimics. The liposome may be reversibly masked to bypass non-target organs. In one example, reversible masking may be accomplished by coating the liposomes with small molecular weight lipids (about 500 Mol. Wt. and lower) such as n-dodecyl-β-D-maltopyranoside. In another embodiment of the present invention, the compacted DNA nanoparticle and liposome delivery systems may be combined. Accordingly, compacted DNA nanoparticles containing the shRNA expression vector may be encapsulated in liposomes. These compacted DNA-nanoparticle-containing liposomes may be BIVs. The liposomes may be decorated with targeting moieties, and may also be reversibly masked.

Another embodiment of the invention is a method to deliver a shRNA to a target tissue expressing PDX-1 comprising the steps of (i) preparing an expression vector comprising a promoter, and an insert of nucleic acid operably linked to the promoter encoding one or more shRNA capable of hybridizing to a region of an mRNA transcript encoding PDX-1; (ii) combining the expression vector with a therapeutic agent carrier; and, (iii) administering a therapeutically effective amount of the expression vector and therapeutic agent carrier complex to a patient in need thereof. The therapeutic agent carrier may be a compacted DNA nanoparticle. In one embodiment, the DNA of the expression vector may be compacted by combining it with polycations. More particularly, the DNA may be compacted by combining it with $CK_{30}PEG10k$. The therapeutic agent carrier may also be a liposome. In one embodiment, the liposome may be a BIV. The liposome may be specifically targeted to a target tissue by decorating it with "smart" receptor targeting moieties. In one example, the targeting moieties may be small molecule bivalent beta-turn mimics. The liposome may be reversibly masked to bypass non-target organs. In one example, reversible masking may be accomplished by coating the liposomes with small molecular weight lipids (about 500 Mol. Wt. and lower) such as n-dodecyl-β-D-maltopyranoside. In another embodiment of the present invention, the compacted DNA nanoparticle and liposome delivery systems may be combined. Thus, compacted DNA nanoparticles containing the shRNA expression vector may be encapsulated in liposomes. These compacted DNA-nanoparticle-containing liposomes may be BIVs. The liposomes may be decorated with targeting moieties, and may also be reversibly masked. In one aspect the one or more shRNA comprise a sequence selected from the group consisting of SEQ. ID NO: 3, SEQ. ID NO: 4, SEQ. ID NO: 5, SEQ. ID NO: 6, SEQ. ID NO: 7, SEQ. ID NO: 8, and combinations or modifications thereof.

The present invention also provides a method to silence the expression of PDX-1 in target cells, the method comprising the steps of (i) selecting a target cell; and (ii) transfecting the target cell with a vector that expresses one or more shRNA capable of hybridizing to a region of an mRNA transcript encoding PDX-1, wherein transfection of cancer cells with the vector inhibits PDX-1 expression via RNA interference. The shRNA may be bifunctional, incorporating simultaneously cleavage-dependent and cleavage-independent motifs. In one embodiment of the present invention, the shRNA is both the cleavage-dependent and cleavage-independent inhibitor of PDX-1 expression. The mRNA sequences targeted by the shRNA are not limited to the 3' untranslated (UTR) region of the PDX-1 mRNA transcript; in one embodiment of the present invention, the shRNA may target coding sequences. The one or more shRNA comprise a sequence selected from the group consisting of SEQ. ID NO: 3, SEQ. ID NO: 4, SEQ. ID NO: 5, SEQ. ID NO: 6, SEQ. ID NO: 7, SEQ. ID NO: 8, and combinations or modifications thereof.

The present invention also includes a method of suppressing tumor cell growth in a cancer patient comprising the steps of (i) identifying a patient in need of treatment of a tumor; and (ii) transfecting the tumor cell with a vector that expresses one or more shRNA capable of hybridizing to a region of an mRNA transcript encoding PDX-1, wherein cancer cells transfected with the vector undergo apoptosis, arrested proliferation, or reduced invasiveness. The shRNA may be bifunctional, incorporating simultaneously cleavage-dependent and cleavage-independent motifs and comprises a sequence selected from the group consisting of SEQ. ID NO: 3, SEQ. ID NO: 4, SEQ. ID NO: 5, SEQ. ID NO: 6, SEQ. ID NO: 7, SEQ. ID NO: 8, and combinations or modifications thereof In one embodiment of the present invention, the shRNA is both the cleavage-dependent and cleavage-independent inhibitor of PDX-1 expression. The mRNA sequences targeted by the shRNA are not limited to the 3' untranslated (UTR) region of the PDX-1 mRNA transcript; in one embodiment of the present invention, the shRNA may target coding sequences. More particularly, the targeted cancer may be a pancreatic neuroendocrine tumor (NET).

BRIEF DESCRIPTION OF THE DRAWINGS

For a more complete understanding of the features and advantages of the present invention, reference is now made to the detailed description of the invention along with the accompanying figures and in which:

FIG. 1A shows the inhibition observed when a single intratumoral injection of bi-shRNA$^{STMN1}$ lipoplex (pGBI2) or scrambled control lipoplex (pGBI5) or suspension solution (D5W) was administered to CCL-247 tumor xenografts. Value represents mean±SEM, FIG. 1B shows the growth inhibitory activity of bi-shRNA$^{S-TMN1}$ on primary osteosarcoma xenografts in SCID mice. Six daily intratumoral injections of bi-sh-RNA$^{STMN1}$ lipoplex or control were administered;

FIGS. 3A and 3B show the effects of bi-functional shRNA on over-expressed human (FIG. 3A) and mouse (FIG. 3B) PDX1 mRNA (SEQ. ID NOS. 1 and 2). Colon cancer CCL-247 cells were either transfected with PDX-1 cDNA expression vector only or co-transfected with PDX-1 cDNA and bi-shRNA expression vectors. pUMVC3 is the expression vector without insert control (SEQ. ID NO: 9). At 24, 48, 72 and 96 hrs post transfection, total RNA were isolated for qRT-PCR. PDX-1 mRNA level was normalized to GAPDH mRNA. Comparative PDX-1 mRNA level for each sample was normalized to media only sample (without transfection);

FIG. 4 shows the silencing effect of bi-functional shRNA on human PDX-1 (SEQ. ID NO: 1). Colon cancer CCL-247 cells were either transfected with species specific PDX-1 cDNA expression vector only or co-transfected with species specific PDX-1 cDNA and bisRNA expression vectors. pUMVC3 is the control expression vector without insert. At 48, 72 and 96 hrs post transfection, cells were harvested for western immunoblot with monoclonal antibody specific for PDX-1 and for β-actin;

FIG. 6A shows the effect on lung, FIG. 6B shows the effect on heart, and FIG. 6C shows the effect on liver. Reduced nonspecific localization in the lungs (FIG. 6A) and heart (FIG. 6B) are seen with increased masking following intravenous injection in BALB/c mice. Masking is associated with enhanced CAT reporter gene localization to intended targeting site (liver; FIG. 6C);

FIG. 7A shows electron micrographs of DNA nanoparticles compacted as ellipsoids or rods. Bar equals 100 nm, FIG. 7B shows liposome mixtures of naked or compacted DNA were added to log phase or growth arrested neuroblastoma cells. Compacted DNA improves gene expression >1000-fold in post-mitotic cells and 6-8-fold in log phase cells, and FIG. 7C. Compacted DNA gene transfer in SCID mice bearing a colon cancer flank explant, dosed either IV or as an intratumoral (IT) injection. IT injection generated high levels of luciferase activity whereas IV dosing did not;

FIG. 8 shows the sequence specificity on the reduction of PDX-1 protein expression at 48 hrs post transfection; colon cancer CCL-247 cells were either transfected with species specific PDX-1 cDNA expression vector only or co-transfected with species specific PDX-1 cDNA and bisRNA expression vectors. pUMVC3 is the control expression vector without insert. At 48 hrs post transfection, cells were harvested for western immunoblot with monoclonal antibody specific for PDX-1 and for β-actin;

FIGS. 9A and 9B show the blood glucose level of SCID mouse xenograft model over time after treatment with bi-shRNA-PDX-1 lipoplex in vivo: β-TC-6 cell insulinoma model (FIG. 9A) and PANC-1 pancreatic cancer model (FIG. 9B). SCID mice were implanted with tumor cells for two weeks before treatment with 3 cycles of 50 μg of bi-shRNA-PDX-1 lipoplex. Fasting blood glucose levels of treated and untreated mice were monitored at regular intervals for up to 90 days post treatment;

DETAILED DESCRIPTION OF THE INVENTION

Figure 1A:
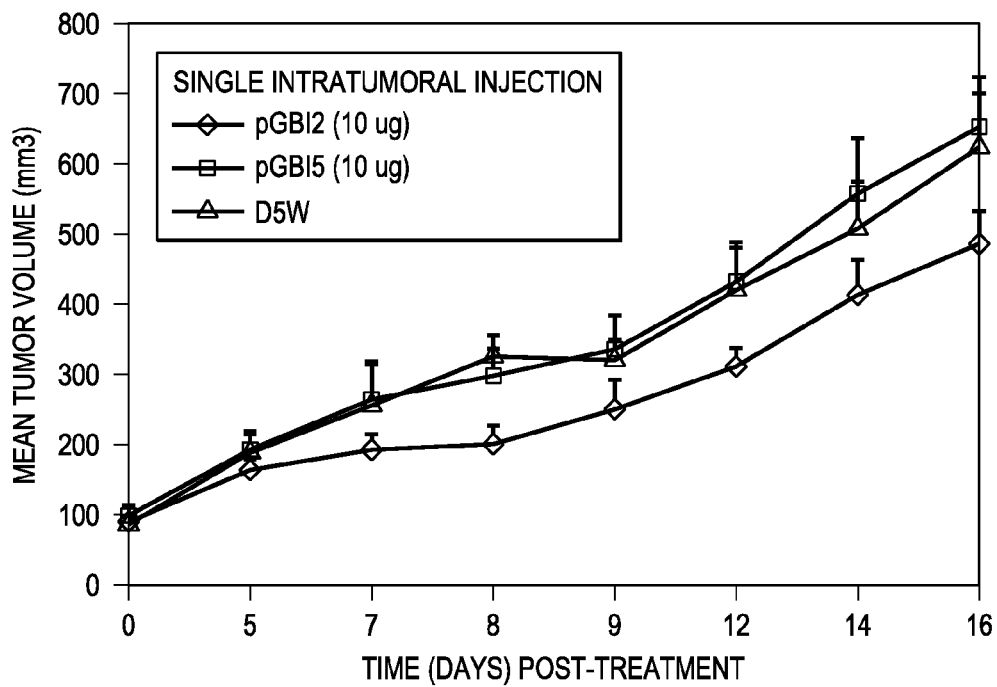
FIGS. 1A and 1B show the in vivo growth inhibitory activities of the bi-shRNA$^{STMN1}$ vector.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein the term "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "expression vector" as used herein in the specification and the claims includes nucleic acid molecules encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter. The term "promoter" refers to any DNA sequence which, when associated with a structural gene in a host yeast cell, increases, for that structural gene, one or more of 1) transcription, 2) translation or 3) mRNA stability, compared to transcription, translation or mRNA stability (longer half-life of mRNA) in the absence of the promoter sequence, under appropriate growth conditions.

The term "oncogene" as used herein refers to genes that permit the formation and survival of malignant neoplastic cells (Bradshaw, T. K.: Mutagenesis 1, 91-97 (1986).

As used herein the term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

The term "hybridizing" refers to any process by which a strand of nucleic acid binds with a complementary strand through base pairing.

The term "transfection" refers to the introduction of foreign DNA into eukaryotic cells. Transfection may be accomplished by a variety of means known to the art including, e.g., calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "liposome" refers to a closed structure composed of lipid bilayers surrounding an internal aqueous space. The term "polycation" as used herein denotes a material having multiple cationic moieties, such as quaternary ammonium radicals, in the same molecule and includes the free bases as well as the pharmaceutically-acceptable salts thereof.

The present invention includes a PDX bi-shRNA developed for the purpose of concurrently inducing translational repression and post-transcriptional mRNA degradation of its target. The prototype construct achieves higher efficacy and prolonged activity as compared to siRNAs with the same mRNA target specificity. The inventors have shown that PDX-1 knockdown induces apoptosis, arrests proliferation, and reduces invasiveness of NET cancer cells, and improves survival of SCID mice bearing carcinoma xenografts. The inventors have also demonstrated that multiple treatments of IV (intravenous) BIV liposomal PDX-1 shRNA resulted in near complete ablation of human PC xenografts in SCID mice and have confirmed response and survival advantage in a murine insulinoma model.

bi-shRNA: The present inventors have pioneered a third unique RNAi platform known as bi-functional shRNA. Conceptually, RNAi can be achieved through shRNA-loaded RISCs to promote cleavage-dependent or cleavage-independent mRNA knockdown. Concomitant expression of both configurations of shRNAs (hence the nomenclature, bi-functional shRNA) has been shown by us to achieve more effective target gene knockdown at a more rapid onset of silencing (rate of mRNA and protein turnover notwithstanding) with greater durability as compared with siRNA. The basic design of the bi-functional shRNA expression unit comprises two stem-loop shRNA structures; one composed of fully matched passenger and guide strands for cleavage-dependent RISC loading, and a second stem-loop with a mismatched passenger strand (at positions 9-12) for cleavage-independent RISC loading. This bi-functional design is, much more efficient for two reasons; first, the bi-functional promotes guide strand loading onto distinct RISC types, hence promoting mRNA targeting; second, the presence of cleavage-dependent and cleavage-independent RISCs against the same target mRNA promotes silencing by both degradation and translational inhibition/sequestration processes. The potent gene knockdown effector achieves spatial and temporal control by the multiplexed shRNAs under the control of a single pol II promoter. The platform designed by the present inventors mimics the natural process. Multiple studies by others and the literature support the approach of the present inventors [66-70].

Figure 1B:
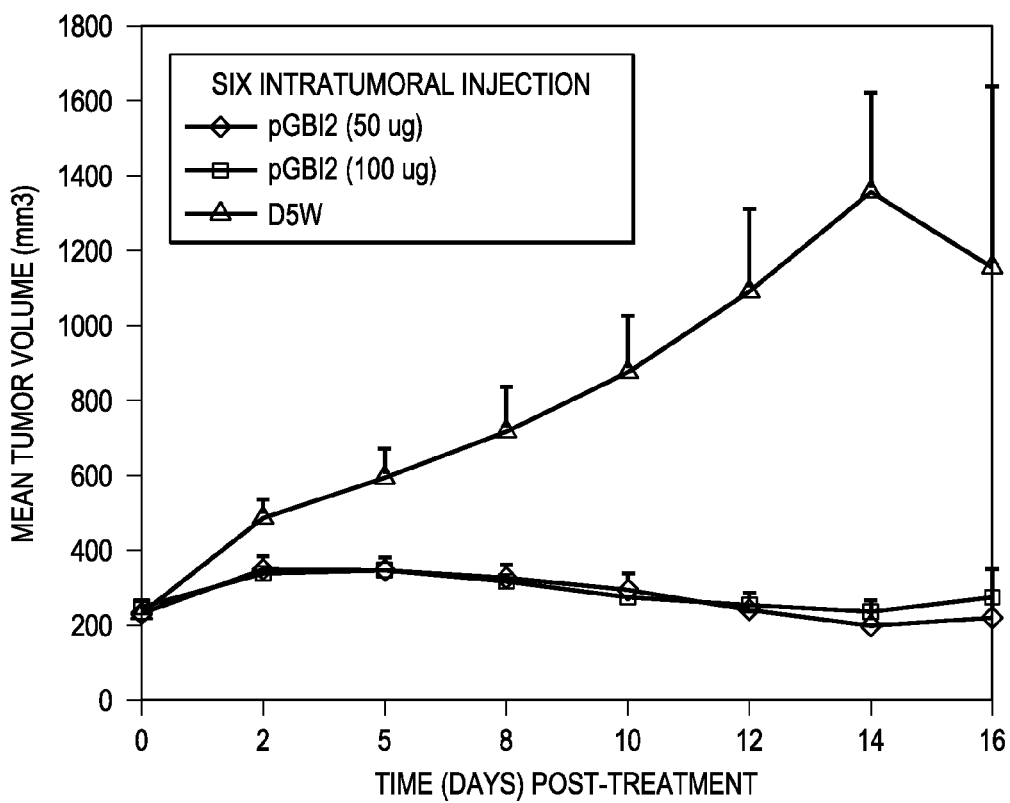

Using a miR30-scaffold, the inventors have produced novel bifunctional (bi-shRNA) against the microtubule remodeling oncoprotein stathmin (STMN1, oncoprotein 18, prosolin, p19, op18). Bi-shRNA$^{STMN1}$ demonstrated more effective silencing activity as compared with siRNAs to the same target site. STMN1 is critically involved in mitotic spindle formation [71, 72]. The bi-shRNA$^{STMN1}$ construct of the present invention demonstrates safe, effective target knockdown and significant dose advantage in tumor cell killing when compared to siRNA to the same target. Moreover, significant tumor growth control and survival advantage was demonstrated by the bi-shRNA$^{STMN1}$ lipoplex in vivo (FIGS. 1A and 1B). The inventors have validated intracellular transcription and processing of both mature and effector molecules (dsRNA with complete matching strands and dsRNA with specified mismatches), using a RT-PCR method that can discriminate between matched and mismatched passenger strands [73]. Most cancer cells have high Drosha and Dicer expression. There has been controversy regarding endogenous Dicer levels in cancer cells [74]. Nonetheless, most studies have indicated that sh or bi-sh RNAi knockdown is highly effective in cancer cells with even low levels of Dicer expression [75]. The present inventors confirmed the expression of the predicted matched and mismatched shRNAs that correspond to mature miRNA/siRNA components to bi-shRNA$^{STMN1}$, as opposed to only having the fully matched passenger stranded in control siRNA$^{STMN1}$ treated cells [76]. To further support the mechanism of the bi-sh RNA$^{STMN1}$, the findings of the studies in the present invention with the 5' RACE method have confirmed the presence of STMN-1 cleavage products with expected sequence corresponding to the target cleavage site of the siRNA (matched) component of the bi-shRNA$^{STMN1}$. Effective knockdown (93%) of STMN1 expressive tumor cells was observed, reflecting the outcome of both cleavage-dependent and independent-mediated knockdowns of the bi-shRNA$^{STMN1}$. Furthermore, STMN1 mRNA kinetics observed following knockdown with the separate component cleavage-dependent (GBI-1) and cleavage-independent (GBI-3) vectors compared to bi-shRNA$^{STMN1}$ (GBI-2) were consistent with predicted mechanism.

Figure 2:
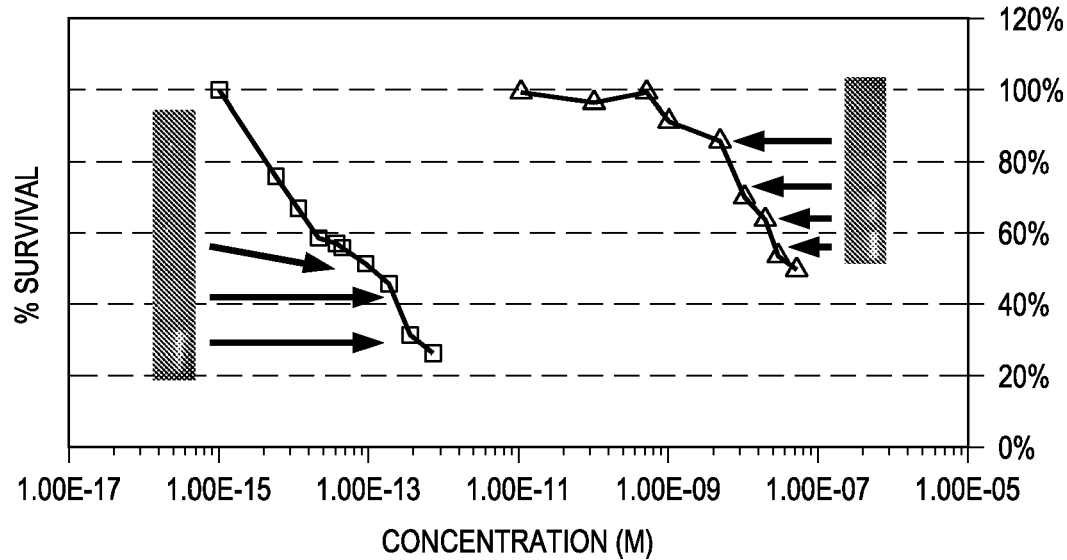
FIG. 2 shows the correlation of STMN1 mRNA target cleavage and cell growth inhibition comparing bi-sh-STMN1 and siRNA$^{STMN1}$. A composite dose response curve for bi-shRNA$^{STMN1}$ (red) and siRNA$^{STMN1}$ (yellow) correlated with STMN1 mRNA cleavage. The x-axis is increasing dose of plasmid/siRNA concentration from left to right. The y-axis is percent cell survival after 24 hours of treatment. Each data point represents the average of triplicate samples. The concentration range of bi-shRNA$^{STMN1}$ varied from $1.44 \times 10^{-12}$ M to $5.63 \times 10^{-15}$ M. The concentration range for siRNA$^{STMN1}$ varied from $5 \times 10^{-7}$ M to $1 \times 10^{-10}$ M. Electropherogram inserts show 5' RACE product detected from transfected CCL-247 cells indicating cleavage product.

Having demonstrated the effector mechanism and functional efficacy of the bi-sh RNA$^{STMN1}$ vector the inventors further explored anticancer activity in vitro and successfully demonstrated effective cell kill in several cancer cell lines. Although targeting to the same sequence, bi-sh RNA$^{STMN1}$ achieved an IC$_{50}$ at 5 logs lower molar concentration than siRNA$^{STMN1}$ (FIG. 2).

Figure 11:
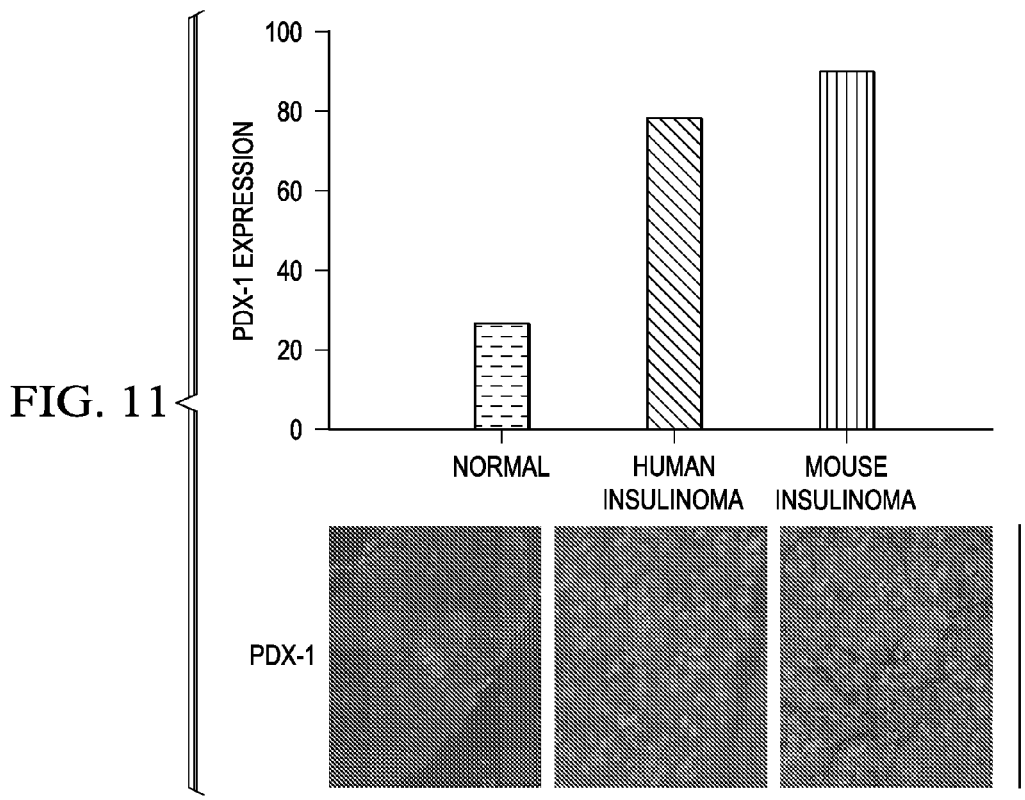
FIG. 11 shows the overexpression of PDX-1 in human insulinoma tumor and mouse TC-6 insulinoma cells.
Figure 12:
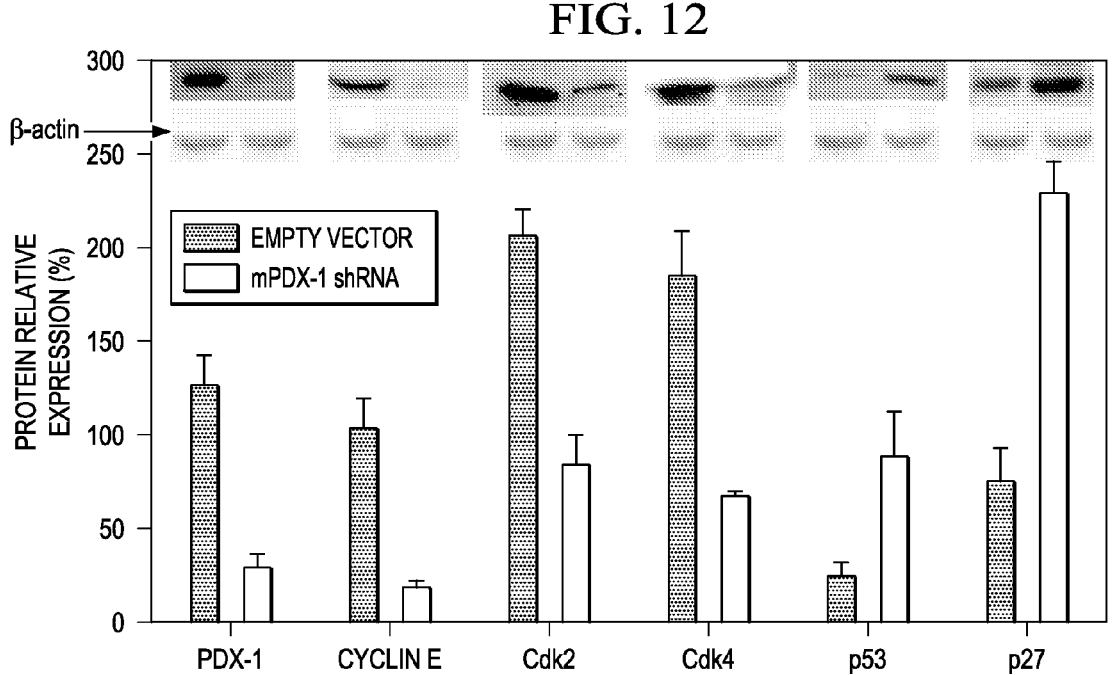
FIG. 12 shows the beta TC-6 cell cycle protein expression after mPDX-1RNA silencing.

Insulinoma is the most common type of islet cell tumor. Malignant insulinomas are devastating from hyperinsulinemia and result in uncontrollable hypoglycemia. As discussed hereinabove pancreatic duodenal homebox-1 (PDX-1) belongs to a homeodomain-containing transcription factor family and plays a primary role in pancreatic organogenesis. PDX-1 maintains beta-cell function by regulating transcription of insulin, glucokinase and glucose transporter type 2. PDX-1 is overexpressed in insulinoma resulting in hyperinsulinemia. PDX-1 is also found to be commonly overexpressed in pancreatic tumors. Metastatic pancreatic cancer has a 4-6 month survival from diagnosis.

shRNA knockdown PDX-1 in mouse insulinoma model: In order to demonstrate expression of PDX-1 in insulinoma, Dr. Brunicardi's lab developed a potent antibody to PDX-1. Using this antibody the present inventors have demonstrated that PDX-1 is significantly over expressed in murine insulinoma to similar levels as in human insulinoma (FIG. 11). The inventors constructed a murine (mu) shRNA to test effect of knockdown in a murine model. Studies are limited however because the lifespan of these mice are 2-3 months due to uncontrollable hypoglycemia as the insulinoma increases in size. In the initial study Beta TC-6 cells were treated with mu-shPDX-1 shRNA in vitro and MTS assay was done to assess cell viability. In comparison to empty vector, mu-shPDX-1 treated cells had substantial reduction in cell proliferation over multiple time points. The inventors further demonstrated that DNA synthesis was significantly reduced at multiple time points with knockdown and demonstrated knockdown by Western blot of several cell cycle relevant proteins in response to PDX-1 knockdown (FIG. 12).

Figure 15:
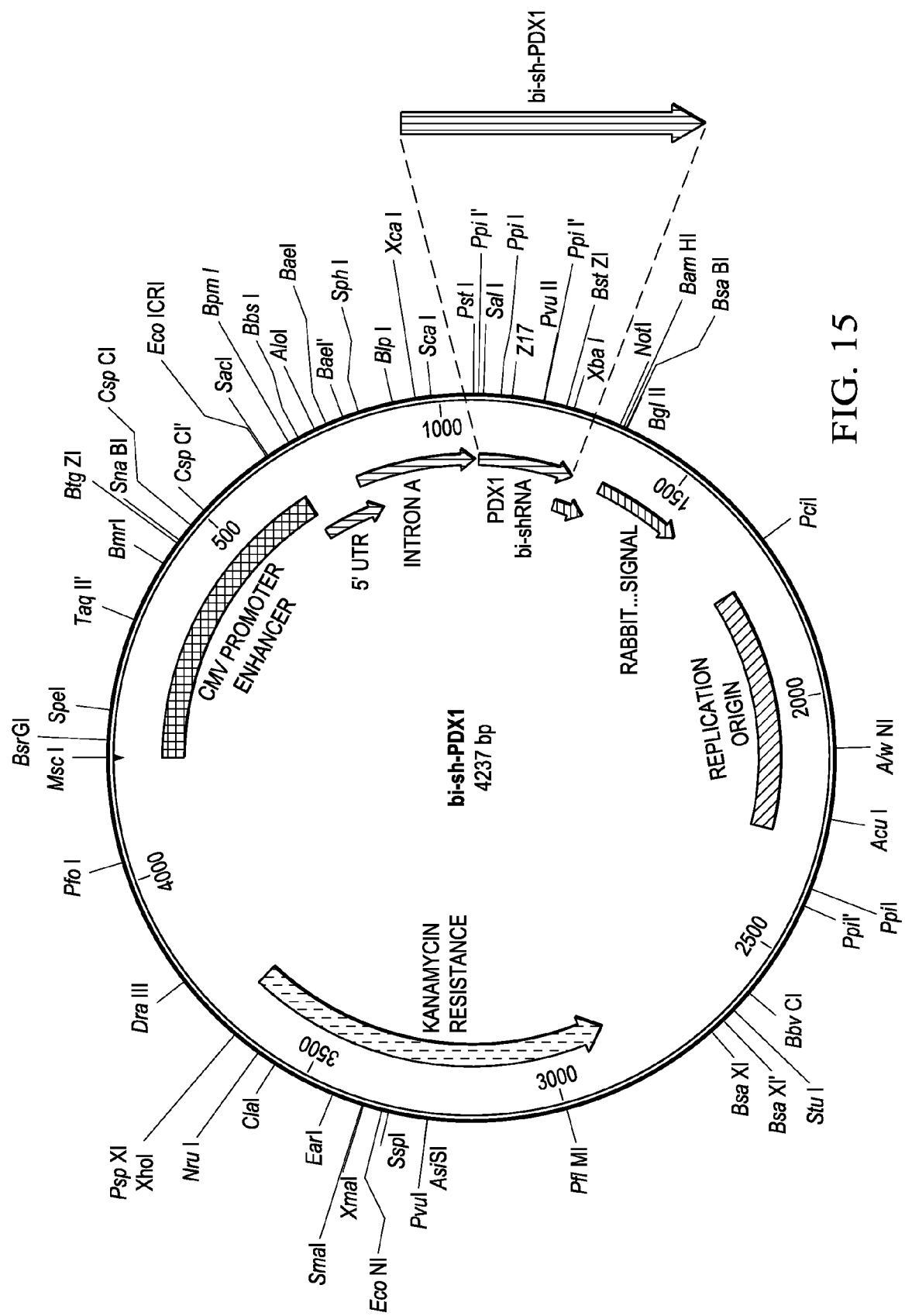
FIG. 15 is a plasmid construct for making the novel bi-shRNA$^{PDX-1}$ of the present invention.

Silencing of PDX-1 expression represents an attractive approach to inhibit tumor growth. The present inventors designed a bi-functional shRNA to silence gene expression of PDX-1. MiR30-based bi-functional shRNA cassettes against either human PDX-1 (SEQ. ID NO: 1) or mouse PDX-1 (SEQ. ID NO: 1) were cloned into pUMVC3 vector. FIG. 15 shows the plasmid construct for making the novel bi-shRNA$^{PDX-1}$. Bi-functional shRNAs targeting mouse or human PDX-1 were co-electroporated into a human colon cancer cell line with expression vectors expressing either mouse or human PDX-1. RACE-PCR was employed to examine potential cleavage products of human and mouse PDX1 mRNA. RT-QPCR and immunoblotting were used to examine the knockdown of expression of either human PDX-1 or mouse PDX-1.

Human pancreatic and duodenal homeobox 1 (PDX1) mRNA (SEQ. ID NO: 1):

```
GGGTGGCGCCGGGAGTGGGAACGCCACACAGTGCCAAATCCCCGGCTCCAGCTCCC
GACTCCCGGCTCCCGGCTCCCGGCTCCCGGTGCCCAATCCCGGGCCGCAGCCATGAA
CGGCGAGGAGCAGTACTACGCGGCCACGCAGCTTTACAAGGACCCCATGCGCGTTCCA
GCGAGGCCCGGCGCCGGAGTTCAGCGCCAGCCCCCCTGCGTGCCTGTACATGGGCC
GCCAGCCCCGGCGCCGGAGTTCAGCGCCAGCCCCCCTGCGTGCCTGTACATGGGCC
GCCAGCCCCGCCGCCGCCGCCGCACCCGTTCCCTGGCGCCCTGGGCGCGCTGGAG
CAGGGCAGCCCCCCGGACATCTCCCCGTACGAGGTGCCCCCCCTCGCCGACGACCCC
GCGGTGGCGCACCTTCACCACCACCTCCCGGCTCAGCTCGCGCTCCCCCACCCGCCC
GCCGGGCCCTTCCCGGAGGGAGCCGAGCCGGGCGTCCTGGAGGAGCCCAACCGCGT
CCAGCTGCCTTTCCCATGGATGAAGTCTACCAAAGCTCACGCGTGGAAAGGCCAGTG
GGCAGGCGGCGCCTACGCTGCGGAGCCGGAGGAGAACAAGCGGACGCGCACGGCCT
ACACGCGCGCACAGCTGCTAGAGCTGGAGAAGGAGTTCCTATTCAACAAGTACATCT
CACGGCCGCGCCGGGTGGAGCTGGCTGTCATGTTGAACTTGACCGAGAGACACATCA
AGATCTGGTTCCAAAACCGCCGCATGAAGTGGAAAAAGGAGGAGGACAAGAAGCGCG
GCGGCGGGACAGCTGTCGGGGCTGGCGGGGTCGCGGAGCCTGAGCAGGACTGCGCC
GTGACCTCCGGCGAGGAGCTTCTGGCGCTGCCGCCGCCGCCGCCCCCCCGGAGGTGCT
GTGCCGCCCGCTGCCCCCGTTGCCGCCCGAGAGGGCCGCCTGCCGCCTGGCCTTAGC
GCGTCGCCACAGCCCTCCAGCGTCGCGCCTCGGCGGCCGCAGGAACCACGATGAGA
GGCAGGAGCTGCTCCTGGCTGAGGGGCTTCAACCACTCGCCGAGGAGGAGCAGAG
GGCCTAGGAGGACCCCGGGCGTGGACCACCCGCCCTGGCAGTTGAATGGGGCGGC
AATTGCGGGGCCCACCTTAGACCGAAGGGGAAAACCCGCTCTCTCAGGCGCATGTG
CCAGTTGGGGCCCCGCGGGTAGATGCCGGCAGGCCTTCCGGAAGAAAAAGAGCCA
TTGGTTTTTGTAGTATTGGGGCCCTCTTTTAGTGATACTGGATTGGCGTTGTTTGTGG
CTGTTGCGCACATCCCTGCCCTCCTACAGCACTCCACCTTGGGACCTGTTTAGAGAA
GCCGGCTCTTCAAAGACAATGGAAACTGTACCATACACATTGGAAGGCTCCCTAAC
ACACACAGCGGGAAGCTGGGCCGAGTACCTTAATCTGCCATAAAGCCATTCTTAC
TCGGGCGACCCCTTTAAGTTTAGAAATAATTGAAAGGAAATGTTTGAGTTTTCAAA
GATCCCGTGAAATTGATGCCAGTGGAATACAGTGAGTCCTCCTCTTCCTCCTCCTCC
TCTTCCCCCTCCCCTTCCTCCTCCTCCTCTTCTTTTCCCTCCTCTTCCTCTTCCTCCTGC
TCTCCTTTCCTCCCCCTCCTCTTTTCCCTCCTCTTCCTCTTCCTCCTGCTCTCCTTTCCT
CCCCCTCCTCTTTCTCCTCCTCCTCCTCTTCTTCCCCCTCCTCTCCCTCCTCCTCTTCTT
CCCCCTCCTCTCCCTCCTCCTCTTCTTCTCCCTCCTCTTCCTCTTCCTCCTCTTCCACG
TGCTCTCCTTTCCTCCCCCTCCTCTTGCTCCCCTTCTTCCCCGTCCTCTTCCTCCTCCT
CCTCTTCTTCTCCCTCCTCTTCCTCCTCCTCTTTCTTCCTGACCTCTTTCTTTCTCCTCC
TCCTCCTTCTACCTCCCCTTCTCATCCCTCCTCTTCCTCTTCTCTAGCTGCACACTTCA
```

-continued

```
CTACTGCACATCTTATAACTTGCACCCCTTTCTTCTGAGGAAGAGAACATCTTGCAA

GGCAGGGCGAGCAGCGGCAGGGCTGGCTTAGGAGCAGTGCAAGAGTCCCTGTGCT

CCAGTTCCACACTGCTGGCAGGGAAGGCAAGGGGGGACGGGCCTGGATCTGGGGG

TGAGGGAGAAAGATGGACCCCTGGGTGACCACTAAACCAAAGATATTCGGAACTTT

CTATTTAGGATGTGGACGTAATTCCTGTTCCGAGGTAGAGGCTGTGCTGAAGACAA

GCACAGTGGCCTGGTGCGCCTTGGAAACCAACAACTATTCACGAGCCAGTATGACC

TTCACATCTTTAGAAATTATGAAAACGTATGTGATTGGAGGGTTTGGAAAACCAGTT

ATCTTATTTAACATTTTAAAAATTACCTAACAGTTATTTACAAACAGGTCTGTGCA

TCCCAGGTCTGTCTTCTTTTCAAGGTCTGGGCCTTGTGCTCGGGTTATGTTTGTGGGA

AATGCTTAATAAATACTGATAATATGGGAAGAGATGAAAACTGATTCTCCTCACTTT

GTTTCAAACCTTTCTGGCAGTGGGATGATTCGAATTCACTTTTAAAATTAAATTAGC

GTGTTTTGTTTTG
```

In the sequence presented hereinabove the coding region is represented in bold italics, and the primary and the secondary target sites represented are underlined and bolded, respectively.

Mouse pancreatic and duodenal homeobox 1 (PDX1) mRNA (SEQ. ID NO: 2):

In the sequence presented hereinabove the coding region is represented in bold italics and the target site represented is underlined.

Figure 3A:
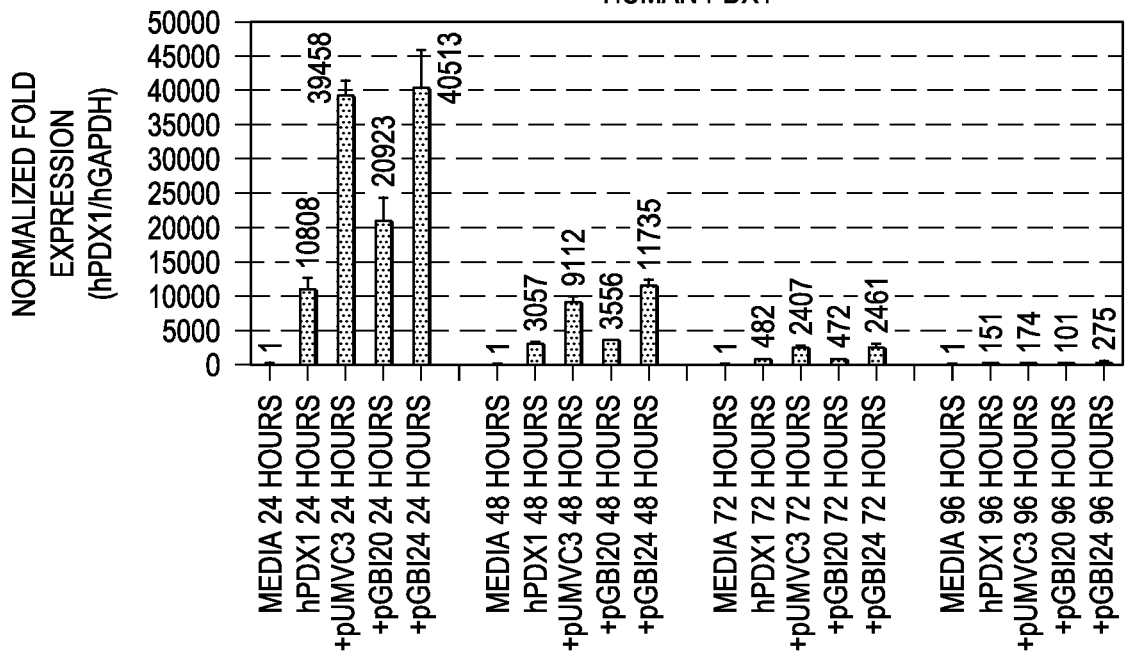

FIGS. 3A and 3B show the effects of bi-functional shRNA on forced over-expressed human and mouse PDX1, respectively. The silencing effect of bi-functional shRNA on human

```
GTCAAAGCGATCTGGGGTGGCGTAGAGAGTCCGCGAGCCACCCAGCGCCTAAGGCC

TGGCTTGTAGCTCCGACCCGGGGCTGCTGGCCCCCAAGTGCCGGCTGCCACC*ATGAA*

*CAGTGAGGAGCAGTACTACGCGGCCACACAGCTCTACAAGGACCCGTGCGCATTCCA*

*GAGGGGCCCGGTGCCAGAGTTCAGCGCTAACCCCCCTGCGTGCCTGTACATGGGCCG*

*CCAGCCCCCACCTCCGCCGCCACCCCAGTTTACAAGCTCGCTGGGATCACTGGAGCA*

*GGGAAGTCCTCCGGACATCTCCCCATACGAAGTGCCCCCGCTCGCCTCCGACGACCC*

*GGCTGGCGCTCACCTCCACCACCACCTTCCAGCTCAGCTCGGGCTCGCCCATCCACCT*

*CCCGGACCTTTCCCGAATGGAACCGAGCCTGGGGGCCTGGAAGAGCCCAACCGCGTC*

*CAGCTCCCTTTCCCGTGGATGAAATCCACCAAAGCTCACGCGTGGAAAGGCCAGTGG*

*GCAGGAGGTGCTTACACAGCGGAACCCGAGGAAAACAAGAGGACCCGTACTGCCTAC*

*ACCCGGGCGCAGCTGCTGGAGCTGGAGAAGGAATTCTTATTTAACAAATACATCTCCC*

*GGCCCCGCCGGGTGGAGCTGGCAGTGATGTTGAACTTGACCGAGAGACACATCAAAA*

*TCTGGTTCCAAAACCGTCGCATGAAGTGGAAAAAAGAGGAAGATAAGAAACGTAGTA*

*GCGGGACCCCGAGTGGGGCGGTGGGGGCGAAGAGCCGGAGCAAGATTGTGCGGTG*

*ACCTCGGGCGAGGAGCTGCTGGCAGTGCCACCGCTGCCACCTCCCGGAGGTGCCGTG*

*CCCCCAGGCGTCCCAGCTGCAGTCCGGGAGGGCCTACTGCCTTCGGGCCTTAGCGTG*

*TCGCCACAGCCCTCCAGCATCGCGCCACTGCGACCGCAGGAACCCGGTGA*GGACAG

CAGTCTGAGGGTGAGCGGGTCTGGGACCCAGAGTGTGGACGTGGGAGCGGGCAGC

TGGATAAGGGAACTTAACCTAGGCGTCGCACAAGAAGAAAATTCTTGAGGGCACG

AGAGCCAGTTGGGTATAGCCGGAGAGATGCTGGCAGACTTCTGGAAAAACAGCCCT

GAGCTTCTGAAAACTTTGAGGCTGCTTCTGATGCCAAGCGAATGGCCAGATCTGCCT

CTAGGACTCTTTCCTGGGACCAATTTAGACAACCTGGGCTCCAAACTGAGGACAAT

AAAAAGGGTACAAACTTGAGCGTTCCAATACGGACCAGC
```

PDX-1 was observed 24 hrs after transfection and lasted for at least 96 hrs (FIG. 4). The maximum silencing effect, 80% knockdown of human PDX-1, was achieved 72 hrs after transfection. Moreover, bi-functional shRNA targeting mouse PDX-1 (with 68% homology to human sequence) did not affect the expression of human PDX-1 (FIG. 8). Similarly, expression of mouse PDX-1 was silenced 24 hrs after transfection and the silencing effects lasted for at least for 96 hrs (FIG. 4). The maximum silencing effect, 95% of mouse PDX-1 expression, was observed 48 hrs after transfection. Moreover, bi-functional shRNAs targeting human PDX-1 (with 79% sequence homology to mouse sequence) did not alter the expression of mouse PDX-1 either (FIG. 8).

Figure 5A:
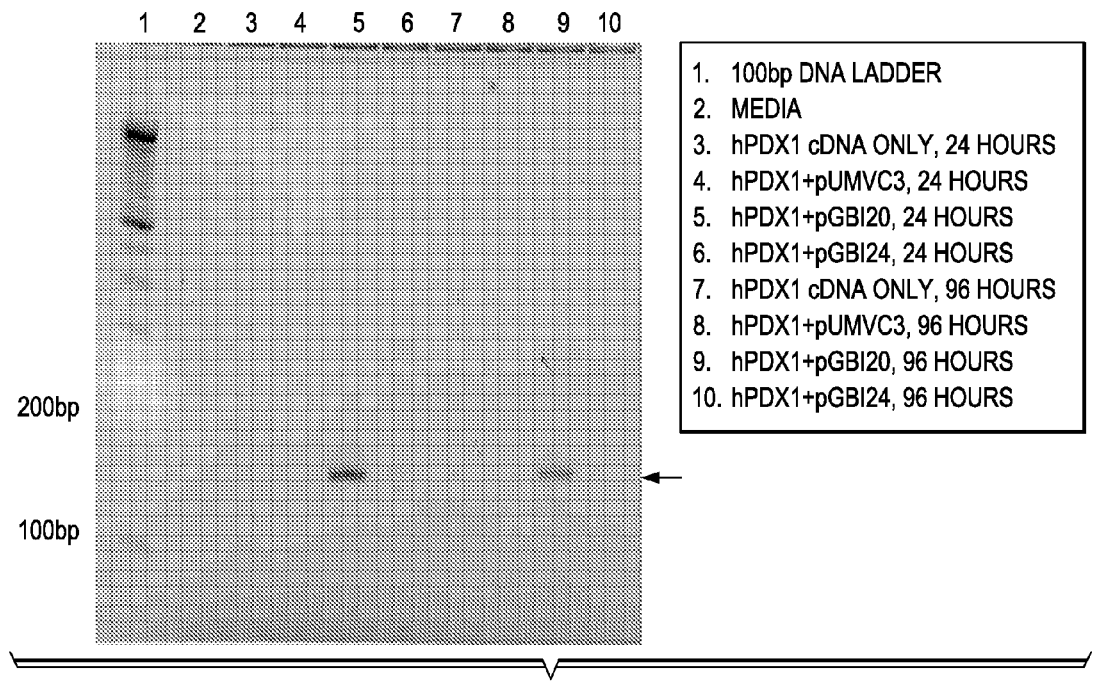
FIGS. 5A and 5B show the identification of target-specific cleavage of human (FIG. 5A) and mouse (FIG. 5B) PDX1 (SEQ. ID NOS. 1 and 2) by RACE-PCR; colon cancer CCL-247 cells were either transfected with PDX-1 cDNA expression vector only or co-transfected with PDX-1 cDNA and bi-shRNA expression vectors. pUMVC3 is the expression vector without insert control. At 24 and 96 hrs post transfection, total RNA were isolated for 5' RACE assay to detect target site cleavage product. RT-PCR amplified cleavage product was shown on agarose gel electropherogram.
Figure 5B:
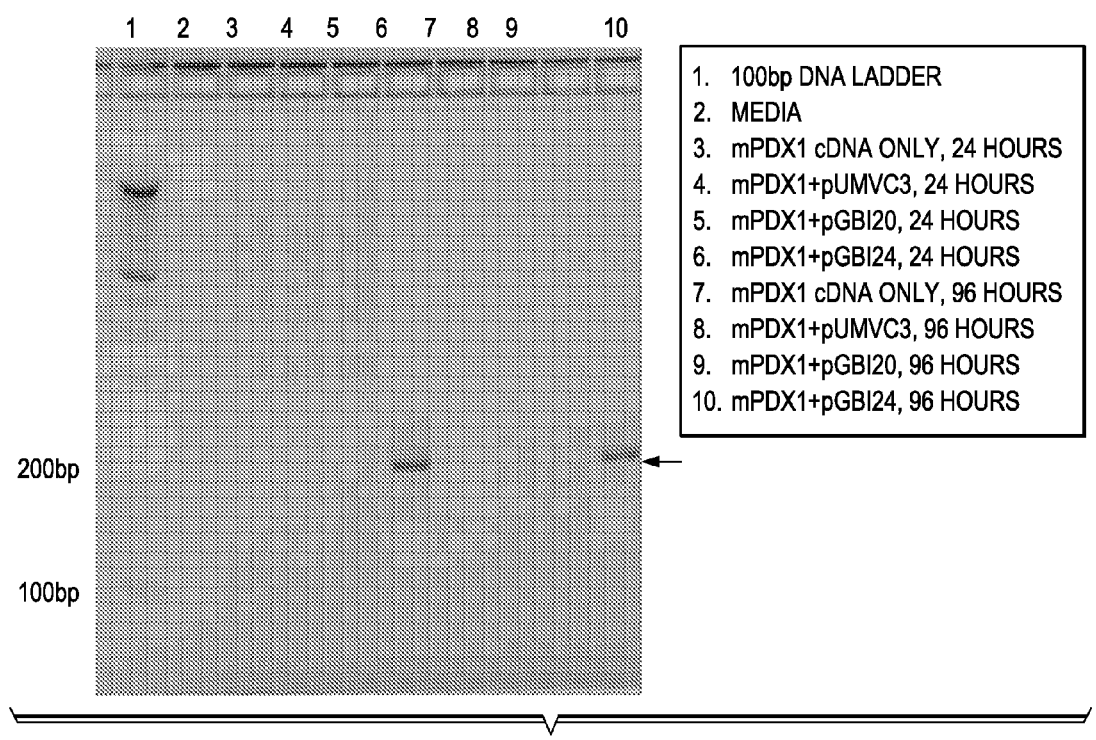

Cleavage products of human and mouse PDX-1 mRNA as identified by RACE-PCR is seen in FIGS. 5A and 5B, respectively. FIGS. 5A and 5B showed that both human PDX1 mRNA and mouse PDX1 mRNA were precisely cleaved in the center of target region as predicted. In addition, the bi-functional shRNA targeting human PDX-1 did not cause the cleavage of the mouse PDX-1 mRNA and vice versa.

The study presented hereinabove demonstrated the efficacy and species-specificity of bi-functional shRNAs targeting either human or mouse PDX1. Bi-shRNA$^{hPDX1}$ knocked down human PDX1 expression and presented no silencing effects on mouse PDX1 expression. Similarly, Bi-shRNA$^{mPDX1}$ knocked down mouse PDX1 expression and presented no silencing effects on human PDX1 expression.

Liposomal delivery system: The liposomal delivery system previously validated by the inventors involved 1,2-dioleoyl-3-trimethyl-ammoniopropane (DOTAP) and cholesterol [77]. This formulation combines with DNA to form complexes that encapsulate nucleic acids within bilamellar invaginated vesicles (liposomal BIVs). One of the inventors has optimized several features of the BIV delivery system for improved delivery of RNA, DNA, and RNAi plasmids. The liposomal BIVs are fusogenic, thereby bypassing endocytosis mediated DNA cell entry, which can lead to nucleic acid degradation [78] and TLR mediated off-target effects. This liposomal delivery system has been used successfully in clinical trial by the present inventors and others [79-83]. Cumulative studies over the last decade indicate that the optimized delivery vehicle needs to be a stealthed (commonly achieved by PEGylation) nanoparticle with a zeta potential of $\leq$10 mV for efficient intravascular transport [84-86] in order to minimize nonspecific binding to negatively-charged serum proteins such as serum albumin (opsonization) [87]. Incorporation of targeting moieties such as antibodies and their single chain derivatives (scFv), carbohydrates, or peptides may further enhance transgene localization to the target cell.

The present inventors have created targeted delivery of the complexes in vivo without the use of PEG thereby avoiding an excessively prolonged circulatory half-life [86, 88-90]. While PEGylation is relevant for DNA or siRNA oligonucleotide delivery to improve membrane permeability, this approach has been shown by the inventors and others to cause steric hindrance in the BIV liposomal structures, resulting in inefficient DNA encapsulation and reduced gene expression. Furthermore, PEGylated complexes enter the cell predominantly through the endocytic pathway, resulting in degradation of the bulk of the nucleic acid in the lysosomes. While PEG provides extremely long half-life in circulation, this has created problems for patients as exemplified by doxil, a PEGylated liposomal formulation that encapsulates the cytotoxic agent doxorubicin [90-92]. Attempts to add ligands to doxil for delivery to specific cell surface receptors (e.g. HER2/neu) have not enhanced tumor-specific delivery [93].

Figure 6A:
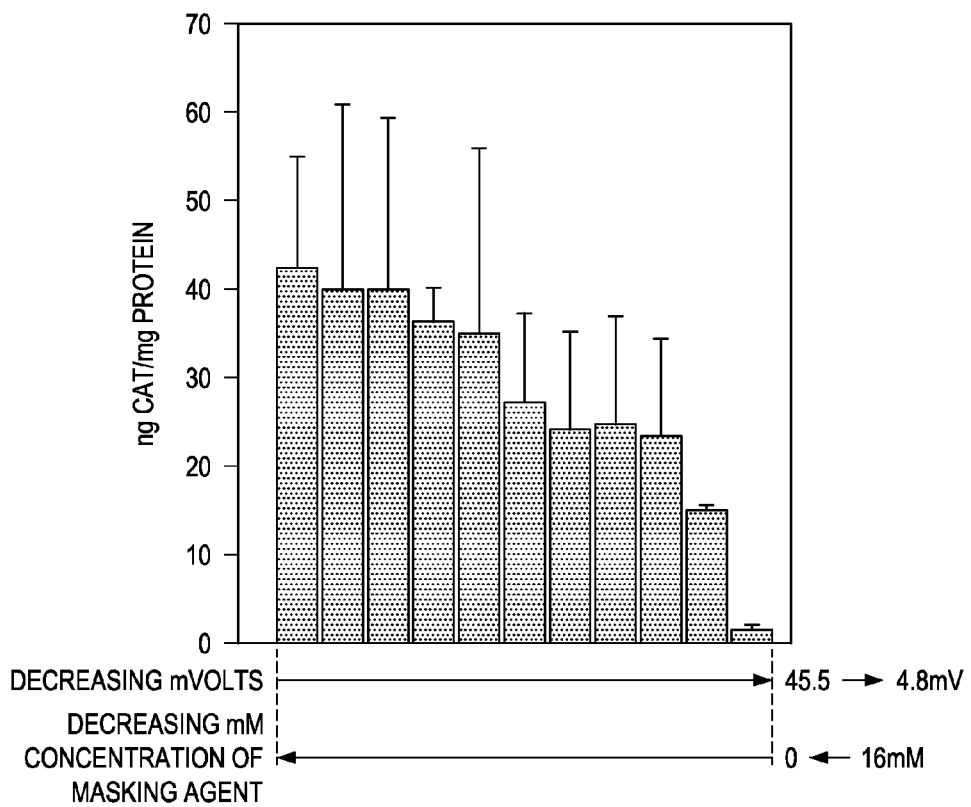
FIGS. 6A-6C show the effect of masking agent on CAT reporter gene production.
Figure 6B:
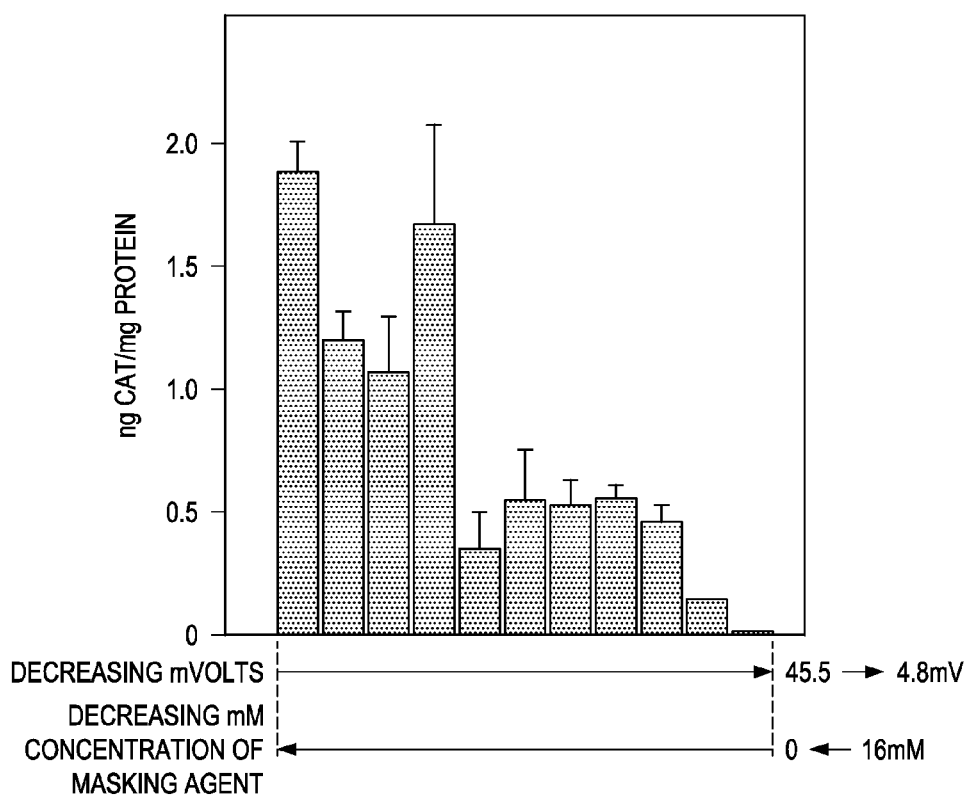
Figure 6C:
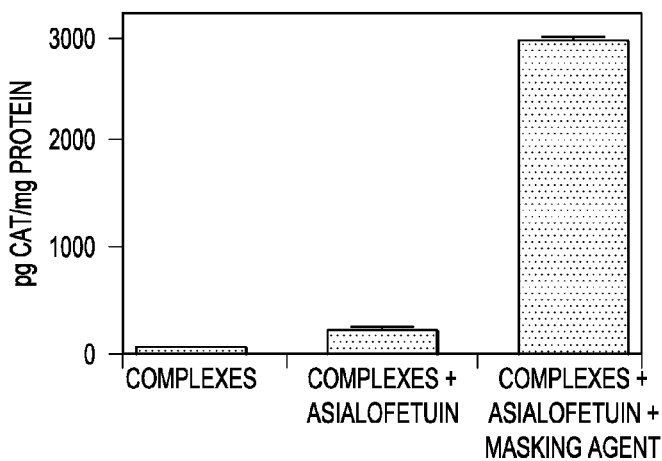

Based on this reasoning, the BIVs of the present invention were produced with DOTAP, and synthetic cholesterol using proprietary manual extrusion process [94]. Furthermore, the delivery was optimized using reversible masking technology. Reversible masking utilizes small molecular weight lipids (about 500 Mol. Wt. and lower; e.g. n-dodecyl-β-D-maltopyranoside) that are uncharged and, thereby, loosely associated with the surface of BIV complexes, thereby temporarily shielding positively charged BIV complexes to bypass non-targeted organs. These small lipids are removed by shear force in the bloodstream. By the time they reach the target cell, charge is re-exposed (optimally ~45 mV) to facilitate entry. FIG. 6A shows the optimization of intravenous lung, and FIG. 6B shows the optimization of intravenous heart transfection with a BIV encapsulating CAT-encapsulating plasmid in BALB/c mice. There was minimal transfection when the reverse masked-complexes circulate systemically, despite having 4.8 mV in charge as measured on a zeta potential analyzer. These complexes reverted to their native charged state (45.5 mV) as masking reversibly dissociates from the BIV complexes, thereby promoting cell entry by membrane fusion and a high level of transgene (CAT) expression in liver hepatocytes (FIG. 6C). Transgene expression was increased by over 100-fold, and nearly matched CAT levels produced in the lungs using the "generic" BIV complexes. Using reversible masking, no CAT production was observed in any other organ.

One reason that our BIV delivery system is uniquely efficient is because the complexes deliver therapeutics into cells by fusion with the cell membrane and avoid the endocytic pathway. The two major entry mechanisms of liposomal entry are via endocytosis or direct fusion with the cell membrane. The inventors found that nucleic acids encapsulated in BIV complexes delivered both in vitro and in vivo enter the cell by direct fusion and that the BIVs largely avoid endosomal uptake, as demonstrated in a comparative study with polyethylene-amine (PEI) in mouse alveolar macrophages. PEI is known to be rapidly and avidly taken up into endosomes, as demonstrated by the localization of $\geq$95% of rhodamine labeled oligonucleotides within 2-3 hrs post-transfection [95-97].

Cancer targeted delivery with decorated BIVs: Recently, Bartlett and Davis showed that siRNAs that were delivered systemically by tumor-targeted nanoparticles (NPs) were significantly more effective in inhibiting the growth of subcutaneous tumors, as compared to undecorated NPs [98]. Targeted delivery did not significantly impact pharmacokinetics or biodistribution, which remain largely an outcome of the EPR (enhanced permeability and retention) effect [95], but appeared to improved transgene expression through enhanced cellular uptake [95-97].

Indeed, a key "missing piece" in development of BIVs for therapeutic use has been the identification of such non-immunogenic ligands that can be placed on the surface of BIV-complexes to direct them to target cells. While it might be possible to do this with small peptides that are multimerized on the surface of liposomes, these can generate immune responses after repeated injections. Other larger ligands including antibodies, antibody fragments, proteins, partial proteins, etc. are far more refractory than using small peptides for targeted delivery on the surface of liposomes. The complexes of the present invention are thus unique insofar as they not only penetrate tight barriers including tumor vasculature endothelial pores and the interstitial pressure gradient of solid tumors [99], but also target tumor cells directly. Therefore, the therapeutic approach of the present invention is not limited to delivery solely dependent on the EPR effect but targets the tumor directly [100-102].

Small molecules designed to bind proteins selectively can be used with the present invention. Importantly, the small molecules prepared are "bivalent" so they are particularly appropriate for binding cell surface receptors, and resemble secondary structure motifs found at hot-spots in protein-ligand interactions. The Burgess group has had success in designing bivalent beta-turn mimics that have an affinity for cell surface receptors [103-105]. The strategy has been adapted by the present inventors to give bivalent molecules that have hydrocarbon tails, and we prepared functionalized BIV complexes from these adapted small molecules. An efficient high throughput technology to screen the library was developed and run.

Figure 7A:
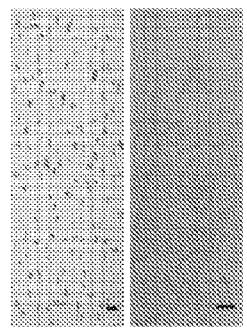
FIGS. 7A-7C shows the structures and functions of compacted DNA nanoparticles.
Figure 7B:
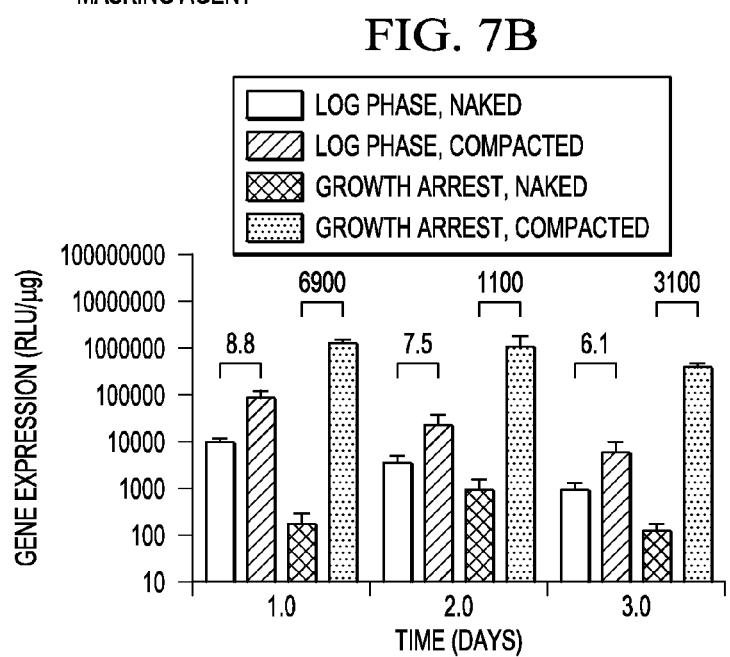

Compacted DNA Nanoparticles: Safe and Efficient DNA Delivery in Post-Mitotic Cells: The Copernicus nucleic acid delivery technology is a non-viral synthetic and modular platform in which single molecules of DNA or siRNA are compacted with polycations to yield nanoparticles having the minimum possible volume [106]. The polycations optimized for in vivo delivery is a 10 kDa polyethylene glycol (PEG) modified with a peptide comprising a N-terminus cysteine and 30 lysine residues ($CK_{30}PEG10k$). The shape of these complexes is dependent in part on the lysine counterion at the time of DNA compaction [107]. The minimum cross-sectional diameter of the rod nanoparticles is 8-11 nm irrespective of the size of the payload plasmid, whereas for ellipsoids the minimum diameter is 20-22 nm for typical expression plasmids (FIG. 7A) [107]. Importantly, these DNA nanoparticles are able to robustly transfect non-dividing cells in culture. Liposome mixtures of compacted DNA generate over 1,000-fold enhanced levels of gene expression compared to liposome naked DNA mixtures (FIG. 7B). Following in vivo dosing, compacted DNA robustly transfects post-mitotic cells in the lung [108], brain [109, 110], and eye [111, 112]. In each of these systems the remarkable ability of compacted DNA to transfect post-mitotic cells appears to be due to the small size of these nanoparticles, which can cross the cross the 25 nm nuclear membrane pore [106].

One uptake mechanism for these DNA nanoparticles is based on binding to cell surface nucleolin (26 nm $K_D$), with subsequent cytoplasmic trafficking via a non-degradative pathway into the nucleus, where the nanoparticles unravel releasing biologically active DNA [113]. Long-term in vivo expression has been demonstrated for as long as 1 year post-gene transfer. These nanoparticles have a benign toxicity profile and do not stimulate toll-like receptors thereby avoiding toxic cytokine responses, even when the compacted DNA has hundreds of CpG islands and are mixed with liposomes, no toxic effect has been observed [114,115]. DNA nanoparticles have been dosed in humans in a cystic fibrosis trial with encouraging results, with no adverse events attributed to the nanoparticles and with most patients demonstrating biological activity of the CFTR protein [116].

Figure 7C:
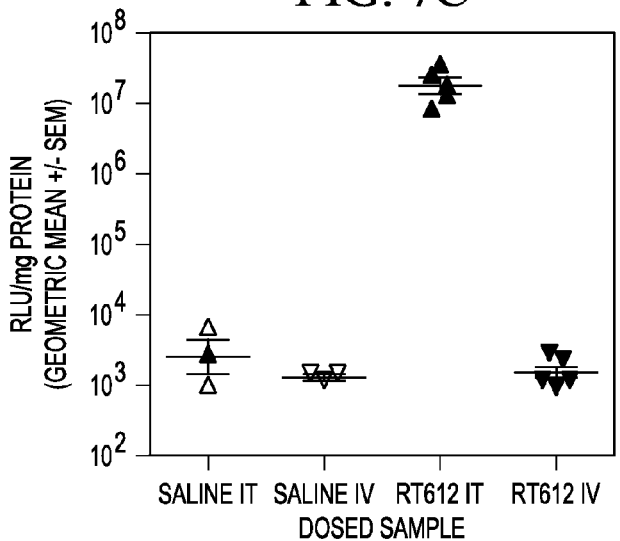

In initial collaborative studies between the present inventors and Copernicus (Cleveland, Ohio), compacted DNA was administered to SCID mice bearing colon cancer tumor explants by either a tail vein or an intratumoral (IT) injection (FIG. 7C). Although IV injection did not produce gene transfer, there was remarkably high level gene transfer following IT dosing, indicating that these DNA nanoparticles are highly active in transfecting tumors after local delivery.

Novel delivery system: Since systemic gene transfer to the primary tumor and metastatic sites is desired, compacted DNA tumor delivery can be facilitated by packaging these nanoparticles comprised of DNA compacted by combining it with a 30 mer lysine condensing peptide in proprietary BIV liposomes. This novel coupling of compacted DNA and masked stealth liposomes represents a novel cancer gene therapy approach.

As seen hereinabove silencing PDX-1 expression by RNA interference in pancreatic cancer cell line PANC-1 inhibited cell proliferation in vitro and suppressed tumor growth in vivo with increased tumor cell apoptosis. Based on this strategy the inventors have developed a bifunctional shRNA (bi-shRNA-PDX-1) for clinical application for the treatment of insulinoma, pancreatic cancer and neuroendocrine tumors. Further the inventors demonstrate efficacy in vitro and efficacy in vivo with insulinoma/SCID model and with PANC-1/SCID pancreatic tumor model.

In vitro knockdown efficacy was assessed by western immunoblot and qRT-PCR analysis of PDX-1 expression in PDX-1 negative human cancer cell line (HCT116) with co-transfection of PDX-1 and bi-shRNA expression vectors (FIGS. 3A, 3B, 4 and 8). Animal models were created by intraperitoneal (IP) injection of $1 \times 10^6$ β-TC-6 cells for in vivo insulinoma model or $5 \times 10^5$ PANC-1 cells for PC model. Two weeks after the inoculation, mice were randomly divided into two groups for each model; one group was given lipoplex (DOTAP:Cholesterol liposome plasmid complex) containing 35 μg of control vector (plasmids without shRNA insert) and the second group was given lipoplex containing 35 μg of either mouse specific bi-msh-PDX-1 (for insulinoma model) or human specific bi-hsh-PDX-1 (for PC model) via tail vein injection. Two repeated deliveries were made every 2 weeks for a total of 3 injections. Blood insulin and glucose levels were monitored at regularly scheduled intervals. At 2 weeks, 10 weeks and 18 weeks after the third injection, 6 mice from each group were killed for pathology and tumor evaluation.

HCT116 human cancer cells were electroporated with 1:1 ratio of plasmids. PDX-1 mRNA was quantitatively compared using qRT-PCR with ΔΔCt method (FIGS. 3A and 3B). The mRNA level was compared to empty vector control to arrive at % expression as summarized in Table 1. PDX-1 mRNA were analyzed at 24, 48 and 72 hrs post transfection.

TABLE 1

Reduction of PDX-1 mRNA expression monitored over 72 hrs post transfection.

|  | 24 hrs | 48 hrs | 72 hrs |
| --- | --- | --- | --- |
| Plasmids |  |  |  |
| hPDX-1 + empty | 100% | 100% | 100% |
| hPDX-1 + hbi-shRNA | 53% | 39% | 20% |
| hPDX-1 + mbi-shRNA | 103% | 129% | 102% |
| Pladmids |  |  |  |
| mPDX-1 + empty | 100% | 100% | 100% |
| mPDX-1 + hbi-shRNA | 75% | 114% | 143% |
| mPDX-1 + mbi-shRNA | 47% | 36% | 24% |

Human and mouse specific bi-shRNA-PDX-1 show effective and species specific knockdown of PDX-1 mRNA expression in vitro.

Blood glucose level of fasting mice was determined at 7 days after each of the first two cycles of treatment, day 45 and day 90. In the mouse insulinoma model treatment with mbi-shRNA-PDX-1 effectively rescued mice from β-TC-6 cell induced hypoglycemia (FIG. 9A) while hbi-shRNA-PDX-1 has no effect on blood glucose level with pancreatic cancer model (FIG. 9B). In the β-TC-6 insulinoma model all untreated mice died before day 90 measurement. The results of PANC-1 pancreatic cancer model are shown in FIG. 9B.

Figure 10A:
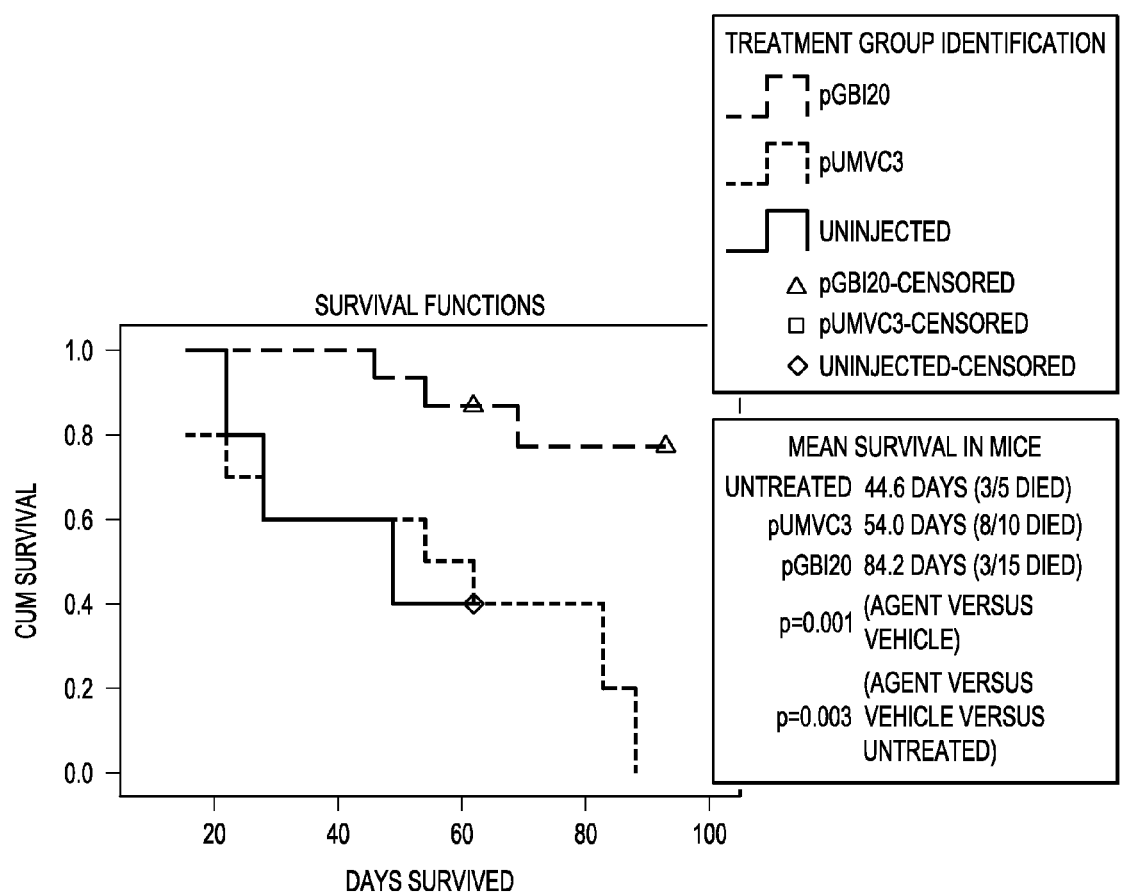
FIGS. 10A and 10B show the Kaplan-Meier Survival analysis: PANC-1 pancreatic cancer model (FIG. 10A) and β-TC-6 cell insulinoma model (FIG. 10B); SCID mice implanted with tumor cells were either not treated or treated with control vector lipoplex (pUMVC3) or with bi-shRNA-PDX-1 lipoplex (3 cycles at 30 μg per cycle). Mice were monitored for survival up to 90 days post treatment.
Figure 10B:
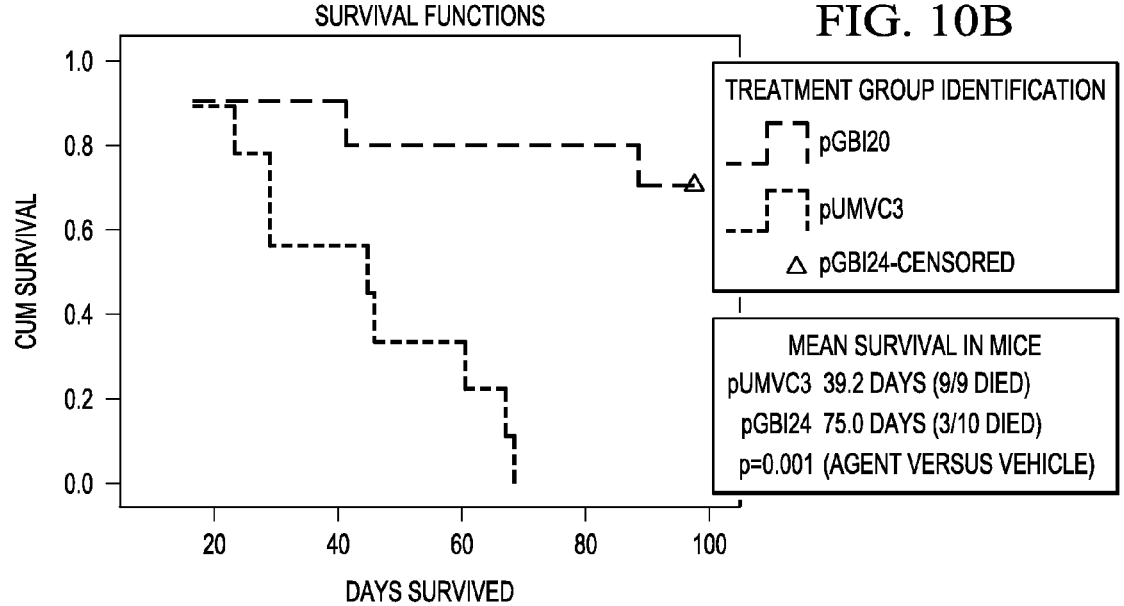
Figure 14:
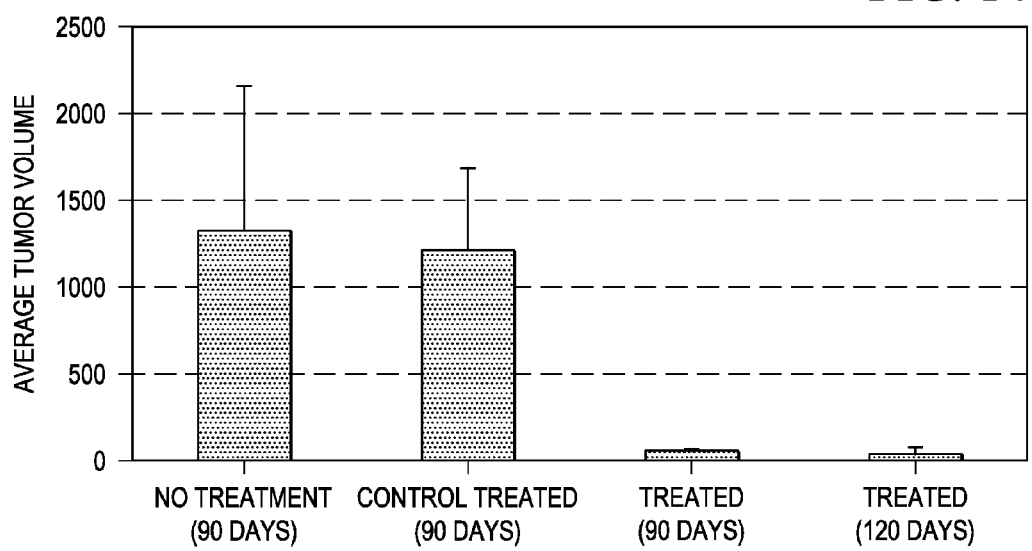
FIG. 14 is a plot showing the tumor volume comparison data.

A Kaplan-Meier Survival analysis further demonstrate benefit of bi-shRNA-PDX-1 treatment for PANC-1 (FIG. 10A) and β-TC-6 insulinoma model (FIG. 10B). For insulinoma model, 10 mice in the treatment group (treated for 3 cycles with 30 ug each of mbi-shRNA-PDX-1 lipoplex and 10 mice in the control group (treated for 3 cycles with 30 ug each of lipoplex containing pUMVC3 vector without bi-shRNA insert) were monitored for survival. The survival was monitored for a period of 95 days. For PC model, 5 PANC-1 inoculated mice were not treated, 10 mice were treated for 3 cycles with 30 ug each of lipoplex containing pUMVC3 vector without bi-shRNA insert and 15 mice were treated for 3 cycles with 30 ug each of hbi-shRNA-PDX-1 lipoplex. 5 mice from each group were sacrificed at day 60 and 90 for tumor volume comparison. At 60 days post treatment, 100% of untreated mice developed tumors with an average of 1330.75 mm³ in size, while only 50% of treated mice had visible tumors with average of 50.5 mm³ in size. At 90 days post treatment, 37.5% of treated mice had no visible tumor and the remainder mice had tumors with an average size of 36.7 mm³. The results of the tumor volume comparison study are presented in Table 2 and are shown in FIG. 14.

Figure 13:
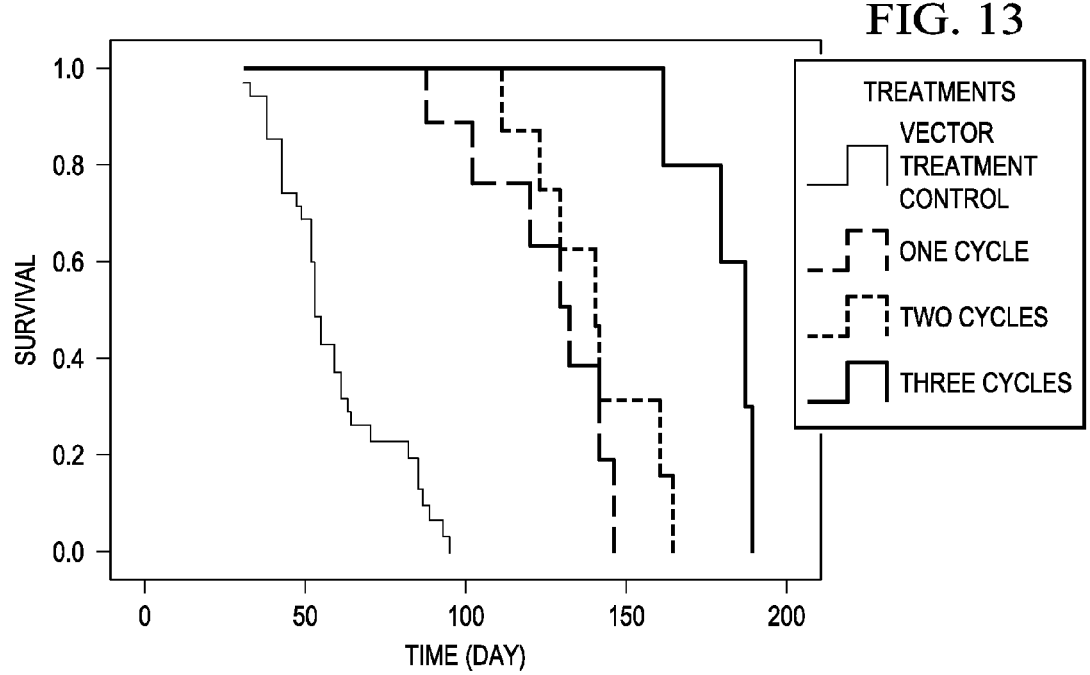
FIG. 13 shows the survival of IV L-mPDX-1 shRNA treated mice in a murine insulinoma SCID model.

Survival was also enhanced in SCID mice following IV infusion of BIV liposomally delivered shRNA$^{PDX-1}$ (L-mu-shRNA$^{PDX-1}$) and appeared to be correlated with the number of L-mu-shRNA$^{PDX-1}$ injections (FIG. 13). The lipoplex (i.e., the lipid-plasmid complex used for the in vivo studies) is denoted by the prefix "L-" to differentiate it from just the vector. Reduced insulin and elevated glucose levels corresponded to L-mu-shRNA$^{PDX-1}$ treatment outcome of insulinoma growth inhibition. Animal tumor responses following treatment with L-mu-shPDX-1 were correlated with detection of PDX-1 knockdown in the insulinoma cells by flow cytometry as well as knockdown of cell cycle proteins (cyclin E, cdk4, cdk2) and upregulation of cyclin dependent kinase inhibitors (p27). Apoptosis was also demonstrated. The inventors have further demonstrated dose related survival advantage in PDX-1 expressive human pancreatic cancer murine xenograft models to IV infusion of shRNA$^{PDX-1}$ lipoplex.

TABLE 2

Tumor volume comparison study.

| Sample | % Tumor | Average Tumor Volume |
| --- | --- | --- |
| 90 day No treatment | 100% | 1330.75 mm³ |
| 90 day Control treatment | 100% | 1199.5 mm³ |
| 90 day treatment | 50% | 50.5 mm³ |
| 120 day treatment | 62.5% | 36.7 mm³ |

Novel bi-shRNA$^{PDX-1}$: To apply the bi-functional shRNA strategy, the present inventors constructed and validated a murine (mu)-bi-shRNA$^{PDX-1}$. The mu-bi-shRNA$^{PDX-1}$ consists of two stem-loop structures with miR-30a backbone. The first stem-loop structure has a complete complementary guide strand and passenger strand, while the second stem-loop structure has two base pair mismatches at positions 10 and 11 of the passenger strand. The mu-bi-shRNA$^{PDX-1}$ is targeted at nucleotides #723-#741 of the mouse PDX-1 mRNA (NM_008814).

The mu-bi-shRNA$^{PDX-1}$ expression unit was assembled together with a combination of oligonucleotides. The assembled expression unit with Sal I and Not I sites at the 5' and 3' ends, respectively, was inserted into the Sal I and Not I sites of pUMVC3. The insert sequences were confirmed by sequencing from both directions with primers flanking the insert. Stem-loop RT-PCR method developed for the detection of microRNA was utilized to detect the mature shRNA in mu-bi-shRNA$^{PDX-1}$ transfected cells. The inventors further validated activity of mu-bi-shRNA$^{PDX-1}$ with the 5' RACE assay to detect target site cleavage.

The insert sequences of the bi-shRNA plasmids of the instant invention are presented herein below:

pGBI-20: Human bi-shRNA-PDX1 (SEQ. ID NO: 3):
TCGACTGCTGTTGAAGTGAGCGCC<u>AGTTCCTATTCAACAAGTA</u>TAGTGA

AGCCACAGATGTATACTTGTTGAATAGGAACTGTTGCCTACTGCCTCGG

AAGCAGCTCACTACATTACTCAGCTGTTGAAGTGAGCGCCAGTTCCTAT

CTAACAAGTATAGTGAAGCCACAGATGTATACTTGTTGAATAGGAACTG

TTGCCTACTGCCTCGGAAGCTTAATAAAGGATCTTTTATTTTCATTGGC

The underlined portion in SEQ. ID NO: 3 (comprising nucleic acid residues from 25 to 43) represents a primary target site.

pGBI-21: Human bi-shRNA-PDX-1 (SEQ. ID NO: 4):
TCGACTGCTGTTGAAGTGAGCGCCAGTTCCTATTCAACAAGTATAGTGA

AGCCACAGATGTATACTTGTTGAATAGGAACTGTTGCCTACTGCCTCGG

AAGCTTAATAAAGGATCTTTTATTTTCATTGGC pGBI-22: human bi-shRNA-PDX-1 (SEQ. ID NO: 5):
TCGACTGCTGTTGAAGTGAGCGCCCAGTTATTTACAAACAGGTTAGTGA

AGCCACAGATGTAACCTGTTTGTAAATAACTGGTTGCCTACTGCCTCGG

AAGCAGCTCACTACATTACTCAGCTGTTGAAGTGAGCGCCCAGTTATTT

CTAAACAGGTTAGTGAAGCCACAGATGTAACCTGTTTGTAAATAACTGG

TTGCCTACTGCCTCGGAAGCTTAATAAAGGATCTTTTATTTTCATTGGC pGBI-23: human bi-shRNA-PDX-1 (SEQ. ID NO: 6):
TCGACTGCTGTTGAAGTGAGCGCCCAGTTATTTACAAACAGGTTAGTGA

AGCCACAGATGTAACCTGTTTGTAAATAACTGGTTGCCTACTGCCTCGG

AAGCTTAATAAAGGATCTTTTATTTTCATTGGC pGBI-24: mouse bi-shRNA-PDX-1 (SEQ ID NO: 7):
TCGACTGCTGTTGAAGTGAGCGC<u>GGAAGATAAGAAACGTAGT</u>TAGTGA

AGCCACAGATGTAACTACGTTTCTTATCTTCCGTTGCCTACTGCCTCGG

AAGCAGCTCACTACATTACTCAGCTGTTGAAGTGAGCGCCGGAAGATAA

ACAACATAGTTAGTGAAGCCACAGATGTAACTACGTTTCTTATCTTCCG

TTGCCTACTGCCTCGGAAGCTTAATAAAGGATCTTTTATTTTCATTGGC

The underlined portion in SEQ. ID NO: 4 (comprising nucleic acid residues from 25 to 43) represents a primary target site.

pGBI-25: mouse bi-shRNA-PDX-1 (SEQ. ID NO: 8):
TCGACTGCTGTTGAAGTGAGCGCGGAAGATAAGAAACGTAGTTAGTGA

AGCCACAGATGTAACTACGTTTCTTATCTTCCGTTGCCTACTGCCTCGG

AAGCTTAATAAAGGATCTTTTATTTTCATTGGC

The construction of a novel bi-shRNA therapeutic of the present invention represents a state-of-the art approach that can reduce the effective systemic dose needed to achieve an effective therapeutic outcome through post-transcriptional gene knockdown. Effective and clinically applicable delivery approaches are in place that can be rapidly transitioned for systemic targeting of PDX-1 overexpressing tumors.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Patent Application No. 2009/0163431: Compositions and Methods for Modulation of PDX-1.
U.S. Pat. No. 6,716,824: Treatment of Pancreatic Adenocarcinoma by Cytotoxic Gene Therapy.
1. Hirshberg, B., et al., Malignant insulinoma: spectrum of unusual clinical features. Cancer, 2005. 104(2): pp. 264-72.
2. Pavelic, K., et al., Molecular genetics of malignant insulinoma. Anticancer Res, 1996. 16(4A): pp. 1707-17.
3. Kaltsas, G. A., G. M. Besser, and A. B. Grossman, The diagnosis and medical management of advanced neuroendocrine tumors. Endocr Rev, 2004. 25(3): pp. 458-511.
4. Pelengaris, S. and M. Khan, Oncogenic co-operation in beta-cell tumorigenesis. Endocr Relat Cancer, 2001. 8(4): pp. 307-14.
5. House, M. G. and R. D. Schulick, Endocrine tumors of the pancreas. Curr Opin Oncol, 2006. 18(1): pp. 23-9.
6. Vezzosi, D., et al., Octreotide in insulinoma patients: efficacy on hypoglycemia, relationships with Octreoscan scintigraphy and immunostaining with anti-sst2A and anti-sst5 antibodies. Eur J Endocrinol, 2005. 152(5): pp. 757-67.
7. Brennan, M. F., Pancreatic cancer. J Gastroenterol Hepatol, 2000. 15 Suppl: pp. G13-6.
8. Urgell, E., et al., Prospective evaluation of the contribution of K-ras mutational analysis and CA 19.9 measurement to cytological diagnosis in patients with clinical suspicion of pancreatic cancer. Eur J Cancer, 2000. 36(16): pp. 2069-75.
9. Willett, C. G., W. J. Daly, and A. L. Warshaw, C A 19-9 is an index of response to neoadjunctive chemoradiation therapy in pancreatic cancer. Am J Surg, 1996. 172(4): pp. 350-2.
10. Blaszkowsky, L., Treatment of advanced and metastatic pancreatic cancer. Front Biosci, 1998. 3: pp. E214-25.
11. Brennan, M., Pancreatic cancer. J. Gastroenterol. Hepatol, 2000. 15: pp. G13-6.
12. Urgell E, P. P., Boadas J, Capella G, Queralto M J M, Boluda R, et al, Prospective evaluation of the contribution of K-ras mutational analysis and CA 19-9 measurement to cytological diagnosis in patients with clinical suspicion of pancreatic cancer Eur. J. Cancer, 2000. 36(16): pp. 2069-2075.
13. Willet C, D. W., Warshaw A., CA19-9 is an index of response to neoadjuvant chemoradiation in pancreatic cancer. Am. J. Surg, 1996. 172: pp. 350-352.

14. Blaszkowsky, L., Treatment of advanced and metastatic pancreatic cancer. Front. Biosci 1998. 3: pp. 214-225.
15. Watada, H., et al., PDX-1 induces insulin and glucokinase gene expressions in alphaTC1 clone 6 cells in the presence of betacellulin. Diabetes, 1996. 45(12): pp. 1826-31.
16. Bretherton-Watt, D., N. Gore, and D. S. Boam, Insulin upstream factor 1 and a novel ubiquitous factor bind to the human islet amyloid polypeptide/amylin gene promoter. Biochem J, 1996. 313 (Pt 2): pp. 495-502.
17. Carty, M. D., et al., Identification of cis- and trans-active factors regulating human islet amyloid polypeptide gene expression in pancreatic beta-cells. J Biol Chem, 1997. 272(18): pp. 11986-93.
18. Serup, P., et al., Induction of insulin and islet amyloid polypeptide production in pancreatic islet glucagonoma cells by insulin promoter factor 1. Proc Natl Acad Sci USA, 1996. 93(17): pp. 9015-20.
19. Watada, H., et al., Involvement of the homeodomain-containing transcription factor PDX-1 in islet amyloid polypeptide gene transcription. Biochem Biophys Res Commun, 1996. 229(3): pp. 746-51.
20. Ballian, N., et al., Proliferation, hyperplasia, neogenesis, and neoplasia in the islets of Langerhans. Pancreas, 2007. 35(3): pp. 199-206.
21. Hagman, D. K., et al., Palmitate inhibits insulin gene expression by altering PDX-1 nuclear localization and reducing MafA expression in isolated rat islets of Langerhans. J Biol Chem, 2005. 280(37): pp. 32413-8.
22. Leys C M, N. S., Rudzinski E, Kaminishi M, Montgomery E, Washington M K, Goldenring J R, Expression of PDX-1 in human gastric metaplasia and gastric adenocarcinoma. Hum Pathol., 2006. 37(9): pp. 1162-8.
23. Sakai H, E. Y., Li X L, Akiyama Y, Miyake S, Takizawa T, Konishi N, Tatematsu M, Koike M, Yuasa Y, PDX-1 homeobox protein expression in pseudopyloric glands and gastric carcinomas. Gut, 2004. 53(3): pp. 323-30.
24. Miyatsuka T, K. H., Shiraiwa T, Matsuoka T A, Yamamoto K, et al, Persistent expression of PDX-1 in the pancreas causes acinar-to-ductal metaplasia through Stat3 activation. Genes Dev, 2006. 20(11): pp. 1435-40.
25. Wang, X. P., et al., Tissue MicroArray analyses of pancreatic duodenal homeobox-1 in human cancers. World J Surg, 2005. 29(3): pp. 334-8.
26. Ayala, G., Prognostic Value of Akt-1 in Prostate Cancer: A Computerized Quantitative Approach with Quantum Dot Technology, in Abstract and presentation. 2007, United States Academy of Pathology: San Diego.
27. Liu, S., et al., PDX-1 acts as a potential molecular target for treatment of human pancreatic cancer. Pancreas, 2008. 37(2): pp. 210-20.
28. Scherr, M., et al., Specific inhibition of bcr-abl gene expression by small interfering RNA. Blood, 2003. 101(4): pp. 1566-9.
29. Brummelkamp, T. R., R. Bernards, and R. Agami, Stable suppression of tumorigenicity by virus-mediated RNA interference. Cancer Cell, 2002. 2(3): pp. 243-7.
30. Martinez, L. A., et al., Synthetic small inhibiting RNAs: efficient tools to inactivate oncogenic mutations and restore p53 pathways. Proc Natl Acad Sci USA, 2002. 99(23): pp. 14849-54.
31. Yoshinouchi, M., et al., In vitro and in vivo growth suppression of human papillomavirus 16-positive cervical cancer cells by E6 siRNA. Mol Ther, 2003. 8(5): pp. 762-8.
32. Choudhury, A., et al., Small interfering RNA (siRNA) inhibits the expression of the Her2/neu gene, upregulates HLA class I and induces apoptosis of Her2/neu positive tumor cell lines. Int J Cancer, 2004. 108(1): pp. 71-7.
33. Yang, G., et al, Inhibition of breast and ovarian tumor growth through multiple signaling pathways by using retrovirus-mediated small interfering RNA against Her-2/neu gene expression. J Biol Chem, 2004. 279(6): pp. 4339-45.
34. Farrow, B., et al., Inhibition of pancreatic cancer cell growth and induction of apoptosis with novel therapies directed against protein kinase A. Surgery, 2003. 134(2): pp. 197-205.
35. Yague, E., C. F. Higgins, and S. Raguz, Complete reversal of multidrug resistance by stable expression of small interfering RNAs targeting MDR1. Gene Ther, 2004. 11(14): pp. 1170-4.
36. Kosciolek, B. A., et al., Inhibition of telomerase activity in human cancer cells by RNA interference. Mol Cancer Ther, 2003. 2(3): pp. 209-16.
37. Cioca, D. P., Y. Aoki, and K. Kiyosawa, RNA interference is a functional pathway with therapeutic potential in human myeloid leukemia cell lines. Cancer Gene Ther, 2003. 10(2): pp. 125-33.
38. Kawasaki, H. and K. Taira, Short hairpin type of dsRNAs that are controlled by tRNA(Val) promoter significantly induce RNAi-mediated gene silencing in the cytoplasm of human cells. Nucleic Acids Res, 2003. 31(2): pp. 700-7.
39. Li, K., et al., Use of RNA interference to target cyclin E-overexpressing hepatocellular carcinoma. Cancer Res, 2003. 63(13): pp. 3593-7.
40. Verma, U. N., et al., Small interfering RNAs directed against beta-catenin inhibit the in vitro and in vivo growth of colon cancer cells. Clin Cancer Res, 2003. 9(4): pp. 1291-300.
41. Aharinejad, S., et al., Colony-stimulating factor-1 blockade by antisense oligonucleotides and small interfering RNAs suppresses growth of human mammary tumor xenografts in mice. Cancer Res, 2004. 64(15): pp. 5378-84.
42. Uchida, H., et al., Adenovirus-mediated transfer of siRNA against survivin induced apoptosis and attenuated tumor cell growth in vitro and in vivo. Mol Ther, 2004. 10(1): pp. 162-71.
43. Salisbury, A. J. and V. M. Macaulay, Development of molecular agents for IGF receptor targeting. Horm Metab Res, 2003. 35(11-12): pp. 843-9.
44. Duxbury, M. S., et al., Focal adhesion kinase gene silencing promotes anoikis and suppresses metastasis of human pancreatic adenocarcinoma cells. Surgery, 2004. 135(5): pp. 555-62.
45. Duxbury, M. S., et al., Systemic siRNA-mediated gene silencing: a new approach to targeted therapy of cancer. Ann Surg, 2004. 240(4): pp. 667-74; discussion 675-6.
46. Filleur, S., et al., SiRNA-mediated inhibition of vascular endothelial growth factor severely limits tumor resistance to antiangiogenic thrombospondin-1 and slows tumor vascularization and growth. Cancer Res, 2003. 63(14): pp. 3919-22.
47. Takei, Y., et al., A small interfering RNA targeting vascular endothelial growth factor as cancer therapeutics. Cancer Res, 2004. 64(10): pp. 3365-70.
48. Lakka, S. S., et al., Inhibition of cathepsin B and MMP-9 gene expression in glioblastoma cell line via RNA interference reduces tumor cell invasion, tumor growth and angiogenesis. Oncogene, 2004. 23(27): pp. 4681-9.
49. Singh, A., et al., RNAi-mediated silencing of nuclear factor erythroid-2-related factor 2 gene expression in non-small cell lung cancer inhibits tumor growth and increases efficacy of chemotherapy. Cancer Res, 2008. 68(19): pp. 7975-84.

50. Nakahira, S., et al., Involvement of ribonucleotide reductase M1 subunit overexpression in gemcitabine resistance of human pancreatic cancer. Int J Cancer, 2007. 120(6): pp. 1355-63.
51. Cullen, B. R., RNAi the natural way. Nat Genet, 2005. 37(11): pp. 1163-5.
52. Zeng, Y. and B. R. Cullen, Sequence requirements for micro RNA processing and function in human cells. RNA, 2003. 9(1): pp. 112-23.
53. Silva, J. M., et al., Second-generation shRNA libraries covering the mouse and human genomes. Nat Genet, 2005. 37(11): pp. 1281-8.
54. Hutvagner, G. and P. D. Zamore, A microRNA in a multiple-turnover RNAi enzyme complex. Science, 2002. 297 (5589): pp. 2056-60.
55. Yekta, S., I. H. Shih, and D. P. Bartel, MicroRNA-directed cleavage of HOXB8 mRNA. Science, 2004. 304(5670): pp. 594-6.
56. Pillai, R. S., C. G. Artus, and W. Filipowicz, Tethering of human Ago proteins to mRNA mimics the miRNA-mediated repression of protein synthesis. Rna, 2004. 10(10): pp. 1518-25.
57. Valencia-Sanchez, M. A., et al., Control of translation and mRNA degradation by miRNAs and siRNAs. Genes Dev, 2006. 20(5): pp. 515-24.
58. Parker, R. and U. Sheth, P bodies and the control of mRNA translation and degradation. Mol Cell, 2007. 25(5): pp. 635-46.
59. (2008) Breakdown of RNAi-Based Drugs in the Clinic. RNAi News Volume.
60. Heidel, J. D., et al., Potent siRNA inhibitors of ribonucleotide reductase subunit RRM2 reduce cell proliferation in vitro and in vivo. Clin Cancer Res, 2007. 13(7): pp. 2207-15.
61. Judge, A. D., et al., Confirming the RNAi-mediated mechanism of action of siRNA-based cancer therapeutics in mice. J Clin Invest, 2009. 119(3): pp. 661-73.
62. Zukiel, R., et al., Suppression of human brain tumor with interference RNA specific for tenascin-C. Cancer Biol Ther, 2006. 5(8): pp. 1002-7.
63. Wyszko, E., et al., A multivariate analysis of patients with brain tumors treated with ATN-RNA. Acta Pol Pharm, 2008. 65(6): pp. 677-84.
64. Calvo, A., et al., Identification of VEGF-regulated genes associated with increased lung metastatic potential: functional involvement of tenascin-C in tumor growth and lung metastasis. Oncogene, 2008. 27(40): pp. 5373-84.
65. Heidel, J. D., et al., Administration in non-human primates of escalating intravenous doses of targeted nanoparticles containing ribonucleotide reductase subunit M2 siRNA. Proc Natl Acad Sci USA, 2007. 104(14): pp. 5715-21.
66. Okamura, K., et al., Distinct roles for Argonaute proteins in small RNA-directed RNA cleavage pathways. Genes Dev, 2004. 18(14): pp. 1655-66.
67. Miyoshi, K., et al., Slicer function of Drosophila Argonautes and its involvement in RISC formation. Genes Dev, 2005. 19(23): pp. 2837-48.
68. Tomari, Y., T. Du, and P. D. Zamore, Sorting of Drosophila small silencing RNAs. Cell, 2007. 130(2): pp. 299-308.
69. Forstemann, K., et al., Drosophila microRNAs are sorted into functionally distinct argonaute complexes after production by dicer-1. Cell, 2007. 130(2): pp. 287-97.
70. Landthaler, M., et al., Molecular characterization of human Argonaute-containing ribonucleoprotein complexes and their bound target mRNAs. RNA, 2008. 14(12): pp. 2580-96.
71. Rana, S., et al., Stathmin 1: a novel therapeutic target for anticancer activity. Expert Rev Anticancer Ther, 2008. 8(9): pp. 1461-70.
72. Iancu, C., et al., Effects of stathmin inhibition on the mitotic spindle. J Cell Sci, 2001. 114(Pt 5): pp. 909-16.
73. Chen, C., et al., Real-time quantification of microRNAs by stem-loop RT-PCR. Nucleic Acids Res, 2005. 33(20): pp. e179.
74. Merritt, W. M., et al., Dicer, Drosha, and outcomes in patients with ovarian cancer. N Engl J Med, 2008. 359(25): pp. 2641-50.
75. Senzer, N., D. Rao, and J. Nemunaitis, Letter to the Editor: Does Dicer expression affect shRNA processing? Gene Regulation and Systems Biology (in press).
76. Rao, D. R., Maples, P. B., Senzer, N., Kumar, P., Wang, Z., Pappen, B. O., Yu, Y., Haddock, C., Tong, A., Nemunaitis, J., Bifunctional shRNA: A novel approach of RNA interference. (submitted), 2009.
77. Ruponen M, H. P., Ronkko S, Pelkonen J, Tammi M, Urtti A, Extracellular and intracellular barriers in non-viral gene delivery J Control Release, 2003. 93(2): pp. 213-217.
78. Simberg D, W. A., Barenholz Y, Reversible mode of binding of serum proteins to DOTAP/cholesterol Lipoplexes: a possible explanation for intravenous lipofection efficiency. Hum Gene Ther, 2005. 16(9): pp. 1087-1096.
79. Jay, C., et al., Preclinical Assessment of wt GNE Gene Plasmid for Management of Hereditary Inclusion Body Myopathy 2 (HIBM2). Gene Regulation & Systems Biology, 2008. 2: pp. 243-52.
80. Frank O, R. C., Heberlein C, Neuhoff N v, Schrock E, Schambach A, et al., Tumor cells escape suicide gene therapy by genetic and epigenetic instability. Blood 2004. 104(12): pp. 3543-3539.
81. Ito I, J. L., Tanaka F, Saito Y, Gopalan B, Branch C D, Xu K, Atkinson E N, Bekele B N, Stephens L C, Minna J D, Roth J A, Ramesh R Liposomal vector mediated delivery of the 3p FUS1 gene demonstrates potent antitumor activity against human lung cancer in vivo. Cancer Gene Ther, 2004. 11(11): pp. 733-9.
82. Templeton, N. S., Reversible masking of liposomal complexes for targeted delivery, USPTO, Editor. 2006, Baylor College of Medicine: USA.
83. Phadke, A. P., et al., Safety and in vivo expression of a GNE-transgene: A novel treatment approach for Hereditary Inclusion Body Myopathy-2. Gene Regulation & Systems Biology, 2009. 3: pp. 89-101.
84. Pirollo, K. F. and E. H. Chang, Targeted delivery of small interfering RNA: approaching effective cancer therapies. Cancer Res, 2008. 68(5): pp. 1247-50.
85. Khalil, I. A., et al., Uptake pathways and subsequent intracellular trafficking in nonviral gene delivery. Pharmacol Rev, 2006. 58(1): pp. 32-45.
86. Li, S. D., et al., Tumor-targeted delivery of siRNA by self-assembled nanoparticles. Mol Ther, 2008. 16(1): pp. 163-9.
87. Tong, A. W., et al., Systemic therapeutic gene delivery for cancer: crafting paris' arrow. Curr Gene Ther, 2009. 9(1): pp. 45-60.
88. Simoes, S., et al., Mechanisms of gene transfer mediated by lipoplexes associated with targeting ligands or pH-sensitive peptides. Gene Ther, 1999. 6(11): pp. 1798-807.
89. Simoes, S., et al., Cationic liposomes for gene delivery. Expert Opin Drug Deliv, 2005. 2(2): pp. 237-54.
90. Sapra, P., P. Tyagi, and T. M. Allen, Ligand-targeted liposomes for cancer treatment. Curr Drug Deliv, 2005. 2(4): pp. 369-81.

91. Sapra, P., B., et al., Ligand-targeted liposomes for cancer treatment Liposomal doxorubicin: antitumor activity and unique toxicities during two complementary phase I studies. Curr Drug Deliv J Clin Oncol, 20051995. 213(47): pp. 369-811777-85.
92. Uziely, B., et al., Liposomal doxorubicin: antitumor activity and unique toxicities during two complementary phase I studies. J Clin Oncol, 1995. 13(7): pp. 1777-85.
93. Park, J. W., et al., Tumor targeting using anti-her2 immunoliposomes. J Control Release, 2001. 74(1-3): pp. 95-113.
94. Bartlett, D. W., N. S., et al., Impact of tumor-specific targeting Improved DNA: liposome complexes for increased systemic delivery and dosing schedule on tumor growth inhibition after intravenous administration of siRNA-containing nanoparticlesgene expression. Nat Biotechnol Bioeng, 20081997. 9915(47): pp. 975-85647-52.
95. Kirpotin, D. B., et al., Antibody targeting of long-circulating lipidic nanoparticles does not increase tumor localization but does increase internalization in animal models. Cancer Res, 2006. 66(13): pp. 6732-40.
96. Maeda, N., et al., Enhancement of anticancer activity in antineovascular therapy is based on the intratumoral distribution of the active targeting carrier for anticancer drugs. Biol Pharm Bull, 2006. 29(9): pp. 1936-40.
97. Bartlett, D. W., et al., Impact of tumor-specific targeting on the biodistribution and efficacy of siRNA nanoparticles measured by multimodality in vivo imaging. Proc Natl Acad Sci USA, 2007. 104(39): pp. 15549-54.
98. Bartlett, D. W. and M. E. Davis, Impact of tumor-specific targeting and dosing schedule on tumor growth inhibition after intravenous administration of siRNA-containing nanoparticles. Biotechnol Bioeng, 2008. 99(4): pp. 975-85.
99. Ramesh, R., et al., Successful treatment of primary and disseminated human lung cancers by systemic delivery of tumor suppressor genes using an improved liposome vector. Mol Ther, 2001. 3(3): pp. 337-50.
100. Hashizume, H., et al., Openings between defective endothelial cells explain tumor vessel leakiness. Am J Pathol, 2000. 156(4): pp. 1363-80.
101. Netti, P. A., et al., Effect of transvascular fluid exchange on pressure-flow relationship in tumors: a proposed mechanism for tumor blood flow heterogeneity. Microvasc Res, 1996. 52(1): pp. 27-46.
102. Yuan, F., et al., Vascular permeability and microcirculation of gliomas and mammary carcinomas transplanted in rat and mouse cranial windows. Cancer Res, 1994. 54(17): pp. 4564-8.
103. Feng, Y., et al., Solid-phase SN2 macrocyclization reactions to form beta-turn mimics. Org Lett, 1999. 1(1): pp. 121-4.
104. Bruno, M. A., et al., Long-lasting rescue of age-associated deficits in cognition and the CNS cholinergic phenotype by a partial agonist peptidomimetic ligand of TrkA. J Neurosci, 2004. 24(37): pp. 8009-18.
105. Zaccaro, M. C., et al., Selective small molecule peptidomimetic ligands of TrkC and TrkA receptors afford discrete or complete neurotrophic activities. Chem Biol, 2005. 12(9): pp. 1015-28.
106. Liu, G., et al., Nanoparticles of compacted DNA transfect postmitotic cells. J Biol Chem, 2003. 278(35): pp. 32578-86.
107. Fink, T. L., et al., Plasmid size up to 20 kbp does not limit effective in vivo lung gene transfer using compacted DNA nanoparticles. Gene Ther, 2006. 13(13): pp. 1048-51.
108. Ziady, A. G., et al., Transfection of airway epithelium by stable PEGylated poly-L-lysine DNA nanoparticles in vivo. Mol Ther, 2003. 8(6): pp. 936-47.
109. Yurek, D. M., et al., Long-term transgene expression in the central nervous system using DNA nanoparticles. Mol Ther, 2009. 17(4): pp. 641-50.
110. Yurek, D. M., et al., Compacted DNA nanoparticle gene transfer of GDNF to the rat striatum enhances the survival of grafted fetal dopamine neurons. Cell Transplant, 2009.
111. Farjo, R., et al., Efficient non-viral ocular gene transfer with compacted DNA nanoparticles. PLoS One, 2006. 1: pp. e38.
112. Cai, X., et al., A partial structural and functional rescue of a retinitis pigmentosa model with compacted DNA nanoparticles. PLoS One, 2009. 4(4): pp. e5290.
113. Chen, X., et al., Cell surface nucleolin serves as receptor for DNA nanoparticles composed of pegylated polylysine and DNA. Mol Ther, 2008. 16(2): pp. 333-42.
114. Ziady, A. G., et al., Minimal toxicity of stabilized compacted DNA nanoparticles in the murine lung. Mol Ther, 2003. 8(6): pp. 948-56.
115. Ding, X. -Q., et al., Ocular delivery of compacted DNA-nanoparticles does not elicit toxicity in the mouse retina. Plos One, 2009. In press.
116. Konstan, M. W., et al., Compacted DNA nanoparticles administered to the nasal mucosa of cystic fibrosis subjects are safe and demonstrate partial to complete cystic fibrosis transmembrane regulator reconstitution. Hum Gene Ther, 2004. 15(12): pp. 1255-69.

What is claimed is:

1. An expression vector comprising:
a promoter; and a nucleic acid insert operably linked to the promoter, wherein the insert encodes one or more short hairpin RNAs (shRNA) capable of hybridizing to a mRNA transcript that encodes a PDX-1 oncogene, wherein the one or more shRNA is bifunctional and can inhibit expression of the PDX-1 oncogene through both cleavage-dependent and cleavage-independent RNA interference, and wherein the one or more shRNA is capable of hybridizing to nucleotides 599-617 and/or 2363-2381 of the PDX-1 transcript set forth in SEQ ID NO: 1, or is capable of hybridizing to nucleotides 723-741 of the PDX-1 transcript set forth in SEQ ID NO: 2.

2. The expression vector of claim 1, wherein the shRNA is capable of hybridizing to nucleotides 2393-2381 of SEQ ID NO: 1 or nucleotides 723-741 of SEQ ID NO: 2.

3. A therapeutic delivery system comprising:
a therapeutic agent carrier; and
an expression vector comprising a promoter and a nucleic acid insert operably linked to the promoter, wherein the insert encodes one or more short hairpin RNAs (shRNA) capable of hybridizing to a mRNA transcript that encodes a PDX-1 oncogene, wherein the one or more shRNA is bifunctional and can inhibit expression of the PDX-1 oncogene through both cleavage-dependent and cleavage-independent RNA interference, and wherein the one or more shRNA is capable of hybridizing to nucleotides 599-617 and/or 2393-2381 of the PDX-1 transcript set forth in SEQ ID NO: 1, or is capable of hybridizing to 723-741 of the PDX-1 transcript set forth in SEQ ID NO: 2.

4. The delivery system of claim 3, wherein the therapeutic agent carrier is a compacted DNA nanoparticle.

5. The delivery system of claim 4, wherein the DNA nanoparticle is compacted with one or more polycations.

6. The delivery system of claim 5, wherein the one or more polycations is a 10 kDa polyethylene glycol (PEG)-substituted cysteine-lysine 30-mer peptide (CK30PEG10k).

7. The delivery system of claim 4, wherein the compacted DNA nanoparticle is further encapsulated in a liposome.

8. The delivery system of claim 7, wherein the liposome is a bilamellar invaginated vesicle (BIV).

9. The delivery system of claim 7, wherein the liposome is a reversibly masked liposome.

10. The delivery system of claim 7, wherein the liposome is decorated with one or more receptor targeting moieties.

11. The delivery system of claim 3, wherein the therapeutic agent carrier is a liposome.

12. The delivery system of claim 11, wherein the liposome is a bilamellar invaginated vesicle (BIV) decorated with one or more receptor targeting moieties, wherein the liposome is a reversibly masked liposome.

13. A method to deliver one or more shRNAs to a target tissue expressing a PDX-1 oncogene comprising the steps of:
preparing an expression vector comprising a promoter and a nucleic acid insert operably linked to the promoter wherein the nucleic acid insert encodes one or more short hairpin RNAs (shRNA) capable of hybridizing to a mRNA transcript that encodes a PDX-1 oncogene, wherein the one or more shRNA is bifunctional and can inhibit expression of the PDX-1 oncogene through both cleavage-dependent and cleavage-independent RNA interference, and wherein the one or more shRNA is capable of hybridizing to nucleotides 599-617 and/or 2393-2381 of the PDX-1 transcript set forth in SEQ ID NO: 1, or is capable of hybridizing to 723-741 of the PDX-1 transcript set forth in SEQ ID NO: 2;
combining the expression vector with a therapeutic agent carrier, wherein the therapeutic agent carrier is a liposome decorated with one or more receptor targeting moieties; and
administering a therapeutically effective amount of the expression vector and therapeutic agent carrier complex to a patient in need thereof.

14. The method of claim 13, wherein the therapeutic agent carrier is a compacted DNA nanoparticle.

15. The method of claim 14, wherein the DNA nanoparticle is compacted with one or more polycations, wherein the one or more polycations comprise a 10 kDa polyethylene glycol (PEG)-substituted cysteine-lysine 30-mer peptide (CK30PEG10k) or a 30-mer lysine condensing peptide.

16. The method of claim 14, wherein the compacted DNA nanoparticles are further encapsulated in a liposome, wherein the liposome is a bilamellar invaginated vesicle (BIV) and is decorated with one or more receptor targeting moieties.

17. The method of claim 16, wherein the liposome is a reversibly masked liposome.

18. The method of claim 13, wherein the liposome is a bilamellar invaginated vesicle (BIV).

19. The method of claim 13, wherein the liposome is a reversibly masked liposome.

20. A method to silence expression of a PDX-1 oncogene in one or more target cells comprising the steps of:
selecting one or more target cells; and
transfecting the target cell with an expression vector according to claim 1.

21. The method of claim 20, wherein the shRNA is capable of hybridizing to nucleotides 2393-2381 of SEQ ID NO: 1 or nucleotides 723-741 of SEQ ID NO: 2.

22. A method of suppressing tumor cell growth, treating an islet neoplasia disorder, or both, in a human subject in need comprising the steps of:
identifying the human subject in need of suppression of tumor cell growth, treatment of islet neoplasia, or both; and
administering an expression vector in a therapeutic agent carrier complex to the human subject in an amount sufficient to inhibit expression of a PDX-1 oncogene in the subject, thereby suppressing tumor cell growth or treating islet neoplasia, or both, wherein the expression vector expresses one or more bifunctional short hairpin RNA (shRNA) capable of hybridizing to nucleotides 599-617 and/or 2393-2381 of the PDX-1 transcript set forth in SEQ ID NO: 1, or capable of hybridizing to nucleotides 723-741 of the PDX-1 transcript set forth in SEQ ID NO: 2, wherein hybridization results in an apoptosis, an arrested proliferation, or a reduced invasiveness of the tumor cells, wherein the shRNA can inhibit expression of the PDX-1 transcript through both cleavage-dependent and cleavage-independent RNA interference.

23. The method of claim 22, wherein the islet neoplasia disorders comprise pancreatic neuroendocrine tumors (NET), insulinomas, and carcinoids.

24. The method of claim 22, wherein the shRNA is capable of hybridizing to nucleotides 2393-2381 of SEQ ID NO: 1 or nucleotides 723-741 of SEQ ID NO: 2.

25. The method of claim 22, wherein the islet neoplasia disorder is a pancreatic neuroendocrine tumor (NET).

26. The method of claim 22, wherein the therapeutic agent carrier is a compacted DNA nanoparticle or a reversibly masked liposome decorated with one or more receptor targeting moieties.

27. The method of claim 26, wherein the DNA nanoparticle is compacted with one or more polycations, wherein the one or more polycations is a 10 kDa polyethylene glycol (PEG)-substituted cysteine-lysine 30-mer peptide (CK30PEG 1 Ok) or a 30-mer lysine condensing peptide.

28. The method of claim 26, wherein the reversibly masked liposome is a bilamellar invaginated vesicle (BIV).

29. The method of claim 26, wherein the compacted DNA nanoparticles are further encapsulated in a liposome.

30. The expression vector of claim 1, wherein the nucleic acid insert comprises one or more of SEQ ID NOS 3-8.

31. The therapeutic delivery system of claim 3, wherein the nucleic acid insert comprises one or more of SEQ ID NOS 3-8.

32. The method of claim 13, wherein the nucleic acid insert comprises one or more of SEQ ID NOS 3-8.

33. The method of claim 20, wherein the nucleic acid insert comprises one or more of SEQ ID NOS 3-8.

34. The method of claim 22 wherein, wherein the expression vector comprises one or more of SEQ ID NOS 3-8.

* * * * *

SEQUENCE LISTING

<160> NUMBER OF SEQ ID NOS: 9

<210> SEQ ID NO 1
<211> LENGTH: 2573
<212> TYPE: DNA
<213> ORGANISM: Homo sapiens

<400> SEQUENCE: 1

```
gggtggcgcc gggagtggga acgccacaca gtgccaaatc cccggctcca gctcccgact      60
cccggctccc ggctcccggc tcccggtgcc caatcccggg ccgcagccat gaacggcgag     120
gagcagtact acgcggccac gcagctttac aaggacccat gcgcgttcca gcgaggcccg     180
gcgccggagt tcagcgccag ccccccctgcg tgcctgtaca tgggccgcca gccccgccg      240
```

```
ccgccgccgc acccgttccc tggcgccctg ggcgcgctgg agcagggcag ccccccggac    300
atctccccgt acgaggtgcc cccctcgcc gacgaccccg cggtggcgca ccttcaccac      360
cacctcccgg ctcagctcgc gctccccac ccgcccgccg ggcccttccc ggagggagcc      420
gagccgggcg tcctggagga gcccaaccgc gtccagctgc cttccccatg gatgaagtct     480
accaaagctc acgcgtggaa aggccagtgg gcaggcggcg cctacgctgc ggagccggag     540
gagaacaagc ggacgcgcac ggcctacacg cgcgcacagc tgctagagct ggagaaggag     600
ttcctattca acaagtacat ctcacggccg cgccgggtgg agctggctgt catgttgaac     660
ttgaccgaga gacacatcaa gatctggttc caaaaccgcc gcatgaagtg aaaaaggag      720
gaggacaaga agcgcggcgg cgggacagct gtcggggtg gcggggtcgc ggagcctgag     780
caggactgcg ccgtgacctc cggcgaggag cttctggcgc tgccgccgcc gccgccccc      840
ggaggtgctg tgccgcccgc tgcccccgtt gccgcccgag agggccgcct gccgcctggc    900
cttagcgcgt cgccacagcc ctccagcgtc gcgcctcggc ggccgcagga accacgatga    960
gaggcaggag ctgctcctgg ctgaggggct tcaaccactc gccgaggagg agcagagggc    1020
ctaggaggac cccgggcgtg gaccaccgc cctggcagtt gaatggggcg gcaattgcgg    1080
ggcccacctt agaccgaagg ggaaaacccg ctctctcagg cgcatgtgcc agttggggcc    1140
ccgcgggtag atgccggcag gccttccgga agaaaaagag ccattggttt ttgtagtatt    1200
ggggcctct tttagtgata ctggattggc gttgtttgtg gctgttgcgc acatccctgc     1260
cctcctacag cactccacct tgggacctgt ttagagaagc cggctcttca aagacaatgg    1320
aaactgtacc atacacattg gaaggctccc taacacacac agcggggaag ctgggccgag    1380
taccttaatc tgccataaag ccattcttac tcgggcgacc cctttaagtt tagaaataat    1440
tgaaaggaaa tgtttgagtt ttcaaagatc ccgtgaaatt gatgccagtg aatacagtg     1500
agtcctcctc ttcctcctcc tctcttccc cctccccttc ctcctcctcc tcttcttttc     1560
cctcctcttc ctcttcctcc tgctctcctt tcctccccct cctcttttcc ctcctcttcc    1620
tcttcctcct gctctccttt cctcccccct ctctttctcc tcctcctcct cttcttcccc    1680
ctcctctccc tcctcctctt cttccccctc ctctccctcc tcctcttctt ctccctcctc    1740
ttcctcttcc tcctcttcca cgtgctctcc tttcctcccc ctcctcttgc tccccttctt    1800
ccccgtcctc ttcctcctcc tcctcttctt ctccctcctc ttcctcctcc tctttcttcc    1860
tgacctcttt cttttctcctc ctcctccttc tacctcccct tctcatccct cctcttcctc    1920
ttctctagct gcacacttca ctactgcaca tcttataact tgcaccccctt tcttctgagg    1980
aagagaacat cttgcaaggc agggcgagca gcggcagggc tggcttagga gcagtgcaag    2040
agtccctgtg ctccagttcc acactgctgg cagggaaggc aagggggac gggcctggat     2100
ctggggtga gggagaaaga tggacccctg ggtgaccact aaaccaaaga tattcggaac     2160
tttctattta ggatgtggac gtaattcctg ttccgaggta gaggctgtgc tgaagacaag    2220
cacagtggcc tggtgcgcct tggaaaccaa caactattca cgagccagta tgaccttcac    2280
atctttagaa attatgaaaa cgtatgtgat tggagggttt ggaaaaccag ttatcttatt    2340
taacatttta aaaattacct aacagttatt tacaaacagg tctgtgcatc ccaggtctgt    2400
cttcttttca aggtctgggc cttgtgctcg ggttatgttt gtgggaaatg cttaataaat    2460
actgataata tgggaagaga tgaaaactga ttctcctcac tttgtttcaa acctttctgg    2520
cagtgggatg attcgaattc acttttaaaa ttaaattagc gtgttttgtt ttg           2573
```

<210> SEQ ID NO 2
<211> LENGTH: 1287
<212> TYPE: DNA
<213> ORGANISM: Mus musculus

<400> SEQUENCE: 2

| | | | | | |
|---|---|---|---|---|---|
| gtcaaagcga | tctggggtgg | cgtagagagt | ccgcgagcca | cccagcgcct | aaggcctggc | 60 |
| ttgtagctcc | gacccggggc | tgctggcccc | caagtgccgg | ctgccaccat | gaacagtgag | 120 |
| gagcagtact | acgcggccac | acagctctac | aaggacccgt | gcgcattcca | gaggggcccg | 180 |
| gtgccagagt | tcagcgctaa | ccccctgcg | tgcctgtaca | tgggccgcca | gcccccacct | 240 |
| ccgccgccac | cccagtttac | aagctcgctg | ggatcactgg | agcagggaag | tcctccggac | 300 |
| atctccccat | acgaagtgcc | cccgctcgcc | tccgacgacc | cggctggcgc | tcacctccac | 360 |
| caccaccttc | cagctcagct | cgggctcgcc | catccacctc | ccggaccttt | cccgaatgga | 420 |
| accgagcctg | ggggcctgga | agagcccaac | cgcgtccagc | tcccttccc | gtggatgaaa | 480 |
| tccaccaaag | ctcacgcgtg | gaaaggccag | tgggcaggag | gtgcttacac | agcggaaccc | 540 |
| gaggaaaaca | gaggacccg | tactgcctac | acccgggcgc | agctgctgga | gctggagaag | 600 |
| gaattcttat | ttaacaaata | catctcccgg | ccccgccggg | tggagctggc | agtgatgttg | 660 |
| aacttgaccg | agagacacat | caaaatctgg | ttccaaaacc | gtcgcatgaa | gtggaaaaaa | 720 |
| gaggaagata | agaaacgtag | tagcgggacc | ccgagtgggg | gcggtggggg | cgaagagccg | 780 |
| gagcaagatt | gtgcggtgac | ctcgggcgag | gagctgctgg | cagtgccacc | gctgccacct | 840 |
| cccgagggtg | ccgtgccccc | aggcgtccca | gctgcagtcc | gggagggcct | actgccttcg | 900 |
| ggccttagcg | tgtcgccaca | gccctccagc | atcgcgccac | tgcgaccgca | ggaaccccgg | 960 |
| tgaggacagc | agtctgaggg | tgagcgggtc | tgggacccag | agtgtggacg | tgggagcggg | 1020 |
| cagctggata | agggaactta | acctaggcgt | cgcacaagaa | gaaaattctt | gagggcacga | 1080 |
| gagccagttg | ggtatagccg | gagagatgct | ggcagacttc | tggaaaaaca | gccctgagct | 1140 |
| tctgaaaact | ttgaggctgc | ttctgatgcc | aagcgaatgg | ccagatctgc | ctctaggact | 1200 |
| ctttcctggg | accaatttag | acaacctggg | ctccaaactg | aggacaataa | aaagggtaca | 1260 |
| aacttgagcg | ttccaatacg | gaccagc | | | | 1287 |

<210> SEQ ID NO 3
<211> LENGTH: 245
<212> TYPE: DNA
<213> ORGANISM: Artificial sequence
<220> FEATURE:
<223> OTHER INFORMATION: Synthetic oligonucleotide.

<400> SEQUENCE: 3

| | | | | | |
|---|---|---|---|---|---|
| tcgactgctg | ttgaagtgag | cgccagttcc | tattcaacaa | gtatagtgaa | gccacagatg | 60 |
| tatacttgtt | gaataggaac | tgttgcctac | tgcctcggaa | gcagctcact | acattactca | 120 |
| gctgttgaag | tgagcgccag | ttcctatcta | acaagtatag | tgaagccaca | gatgtatact | 180 |
| tgttgaatag | gaactgttgc | ctactgcctc | ggaagcttaa | taaggatct | tttattttca | 240 |
| ttggc | | | | | | 245 |

<210> SEQ ID NO 4
<211> LENGTH: 131
<212> TYPE: DNA
<213> ORGANISM: Artificial sequence
<220> FEATURE:
<223> OTHER INFORMATION: Synthetic oligonucleotide.

<400> SEQUENCE: 4

```
tcgactgctg ttgaagtgag cgccagttcc tattcaacaa gtatagtgaa gccacagatg      60
tatacttgtt gaataggaac tgttgcctac tgcctcggaa gcttaataaa ggatctttta     120
ttttcattgg c                                                          131
```

<210> SEQ ID NO 5
<211> LENGTH: 245
<212> TYPE: DNA
<213> ORGANISM: Artificial sequence
<220> FEATURE:
<223> OTHER INFORMATION: Synthetic oligonucleotide.

<400> SEQUENCE: 5

```
tcgactgctg ttgaagtgag cgcccagtta tttacaaaca ggttagtgaa gccacagatg      60
taacctgttt gtaaataact ggttgcctac tgcctcggaa gcagctcact acattactca     120
gctgttgaag tgagcgccca gttatttcta aacaggttag tgaagccaca gatgtaacct     180
gtttgtaaat aactggttgc ctactgcctc ggaagcttaa taaggatct tttattttca     240
ttggc                                                                 245
```

<210> SEQ ID NO 6
<211> LENGTH: 131
<212> TYPE: DNA
<213> ORGANISM: Artificial sequence
<220> FEATURE:
<223> OTHER INFORMATION: Synthetic oligonucleotide.

<400> SEQUENCE: 6

```
tcgactgctg ttgaagtgag cgcccagtta tttacaaaca ggttagtgaa gccacagatg      60
taacctgttt gtaaataact ggttgcctac tgcctcggaa gcttaataaa ggatctttta     120
ttttcattgg c                                                          131
```

<210> SEQ ID NO 7
<211> LENGTH: 245
<212> TYPE: DNA
<213> ORGANISM: Artificial sequence
<220> FEATURE:
<223> OTHER INFORMATION: Synthetic oligonucleotide.

<400> SEQUENCE: 7

```
tcgactgctg ttgaagtgag cgccggaaga taagaaacgt agttagtgaa gccacagatg      60
taactacgtt tcttatcttc cgttgcctac tgcctcggaa gcagctcact acattactca     120
gctgttgaag tgagcgccgg aagataaaca acatagttag tgaagccaca gatgtaacta     180
cgtttcttat cttccgttgc ctactgcctc ggaagcttaa taaggatct tttattttca     240
ttggc                                                                 245
```

<210> SEQ ID NO 8
<211> LENGTH: 131
<212> TYPE: DNA
<213> ORGANISM: Artificial sequence
<220> FEATURE:
<223> OTHER INFORMATION: Synthetic oligonucleotide.

<400> SEQUENCE: 8

```
tcgactgctg ttgaagtgag cgccggaaga taagaaacgt agttagtgaa gccacagatg      60
taactacgtt tcttatcttc cgttgcctac tgcctcggaa gcttaataaa ggatctttta     120
ttttcattgg c                                                          131
```

<210> SEQ ID NO 9
<211> LENGTH: 4030
<212> TYPE: DNA
<213> ORGANISM: Artificial sequence
<220> FEATURE:
<223> OTHER INFORMATION: Synthetic oligonucleotide.

<400> SEQUENCE: 9

| | | | | | |
|---|---|---|---|---|---|
| tggccattgc | atacgttgta | tccatatcat | aatatgtaca | tttatattgg | ctcatgtcca | 60 |
| acattaccgc | catgttgaca | ttgattattg | actagttatt | aatagtaatc | aattacgggg | 120 |
| tcattagttc | atagcccata | tatggagttc | cgcgttacat | aacttacggt | aaatggcccg | 180 |
| cctggctgac | cgcccaacga | cccccgccca | ttgacgtcaa | taatgacgta | tgttcccata | 240 |
| gtaacgccaa | tagggacttt | ccattgacgt | caatgggtgg | agtatttacg | gtaaactgcc | 300 |
| cacttggcag | tacatcaagt | gtatcatatg | ccaagtacgc | ccctattga | cgtcaatgac | 360 |
| ggtaaatggc | ccgcctggca | ttatgcccag | tacatgacct | tatgggactt | tcctacttgg | 420 |
| cagtacatct | acgtattagt | catcgctatt | accatgtga | tgcggttttg | gcagtacatc | 480 |
| aatgggcgtg | gatagcggtt | tgactcacgg | ggatttccaa | gtctccaccc | cattgacgtc | 540 |
| aatgggagtt | tgttttggca | ccaaaatcaa | cgggactttc | caaaatgtcg | taacaactcc | 600 |
| gccccattga | cgcaaatggg | cggtaggcgt | gtacggtggg | aggtctatat | aagcagagct | 660 |
| cgtttagtga | accgtcagat | cgcctggaga | cgccatccac | gctgttttga | cctccataga | 720 |
| agacaccggg | accgatccag | cctccgcggc | cgggaacggt | gcattggaac | gcggattccc | 780 |
| cgtgccaaga | gtgacgtaag | taccgcctat | agactctata | ggcacacccc | tttggctctt | 840 |
| atgcatgcta | tactgttttt | ggcttgggc | ctatacaccc | ccgcttcctt | atgctatagg | 900 |
| tgatggtata | gcttagccta | taggtgtggg | ttattgacca | ttattgacca | ctccaacggt | 960 |
| ggagggcagt | gtagtctgag | cagtactcgt | tgctgccgcg | cgcgccacca | gacataatag | 1020 |
| ctgacagact | aacagactgt | tcctttccat | gggtcttttc | tgcagtcacc | gtcgtcgacg | 1080 |
| gtatcgataa | gcttgatatc | gaattcacgt | gggcccggta | ccgtatactc | tagagcggcc | 1140 |
| gcggatccag | atcttttttcc | ctctgccaaa | aattatgggg | acatcatgaa | gccccttgag | 1200 |
| catctgactt | ctggctaata | aaggaaattt | attttcattg | caatagtgtg | ttggaatttt | 1260 |
| ttgtgtctct | cactcggaag | gacatatggg | agggcaaatc | atttaaaaca | tcagaatgag | 1320 |
| tatttggttt | agagtttggc | aacatatgcc | cattcttccg | cttcctcgct | cactgactcg | 1380 |
| ctgcgctcgg | tcgttcggct | gcggcgagcg | gtatcagctc | actcaaaggc | ggtaatacgg | 1440 |
| ttatccacag | aatcagggga | taacgcagga | aagaacatgt | gagcaaaagg | ccagcaaaag | 1500 |
| gccaggaacc | gtaaaaaggc | cgcgttgctg | gcgtttttcc | ataggctccg | cccccctgac | 1560 |
| gagcatcaca | aaaatcgacg | ctcaagtcag | aggtggcgaa | acccgacagg | actataaaga | 1620 |
| taccaggcgt | ttccccctgg | aagctccctc | gtgcgctctc | ctgttccgac | cctgccgctt | 1680 |
| accggatacc | tgtccgcctt | tctcccttcg | ggaagcgtgg | cgctttctca | tagctcacgc | 1740 |
| tgtaggtatc | tcagttcggt | gtaggtcgtt | cgctccaagc | tgggctgtgt | gcacgaaccc | 1800 |
| cccgttcagc | ccgaccgctg | cgccttatcc | ggtaactatc | gtcttgagtc | caacccggta | 1860 |
| agacacgact | tatcgccact | ggcagcagcc | actggtaaca | ggattagcag | agcgaggtat | 1920 |
| gtaggcggtg | ctacagagtt | cttgaagtgg | tggcctaact | acggctacac | tagaagaaca | 1980 |
| gtatttggta | tctgcgctct | gctgaagcca | gttaccttcg | gaaaaagagt | tggtagctct | 2040 |
| tgatccggca | aacaaaccac | cgctggtagc | ggtggttttt | ttgtttgcaa | gcagcagatt | 2100 |
| acgcgcagaa | aaaaaggatc | tcaagaagat | cctttgatct | tttctacggg | gtctgacgct | 2160 |

```
cagtggaacg aaaactcacg ttaagggatt ttggtcatga gattatcaaa aaggatcttc    2220
acctagatcc ttttaaatta aaaatgaagt tttaaatcaa tctaaagtat atatgagtaa    2280
acttggtctg acagttacca atgcttaatc agtgaggcac ctatctcagc gatctgtcta    2340
tttcgttcat ccatagttgc ctgactcggg gggggggggc gctgaggtct gcctcgtgaa    2400
gaaggtgttg ctgactcata ccaggcctga atcgccccat catccagcca gaaagtgagg    2460
gagccacggt tgatgagagc tttgttgtag gtggaccagt tggtgatttt gaactttgc     2520
tttgccacgg aacggtctgc gttgtcggga agatgcgtga tctgatcctt caactcagca    2580
aaagttcgat ttattcaaca aagccgccgt cccgtcaagt cagcgtaatg ctctgccagt    2640
gttacaacca attaaccaat tctgattaga aaaactcatc gagcatcaaa tgaaactgca    2700
atttattcat atcaggatta tcaataccat attttgaaa aagccgtttc tgtaatgaag     2760
gagaaaactc accgaggcag ttccatagga tggcaagatc ctggtatcgg tctgcgattc    2820
cgactcgtcc aacatcaata caacctatta atttcccctc gtcaaaaata aggttatcaa    2880
gtgagaaatc accatgagtg acgactgaat ccggtgagaa tggcaaaagc ttatgcattt    2940
ctttccagac ttgttcaaca ggccagccat tacgctcgtc atcaaaatca ctcgcatcaa    3000
ccaaaccgtt attcattcgt gattgcgcct gagcgagacg aaatacgcga tcgctgttaa    3060
aaggacaatt acaaacagga atcgaatgca accggcgcag gaacactgcc agcgcatcaa    3120
caatattttc acctgaatca ggatattctt ctaatacctg gaatgctgtt ttcccgggga    3180
tcgcagtggt gagtaaccat gcatcatcag gagtacggat aaaatgcttg atggtcggaa    3240
gaggcataaa ttccgtcagc cagtttagtc tgaccatctc atctgtaaca tcattggcaa    3300
cgctacccttt gccatgtttc agaaacaact ctggcgcatc gggcttccca tacaatcgat    3360
agattgtcgc acctgattgc ccgacattat cgcgagccca tttataccca tataaatcag    3420
catccatgtt ggaatttaat cgcggcctcg agcaagacgt ttcccgttga atatggctca    3480
taacacccct tgtattactg tttatgtaag cagacagttt tattgttcat gatgatatat    3540
ttttatcttg tgcaatgtaa catcagagat tttgagacac aacgtggctt tccccccccc    3600
cccattattg aagcatttat cagggttatt gtctcatgag cggatacata tttgaatgta    3660
tttagaaaaa taaacaaata ggggttccgc gcacatttcc ccgaaaagtg ccacctgacg    3720
tctaagaaac cattattatc atgacattaa cctataaaaa taggcgtatc acgaggccct    3780
ttcgtctcgc gcgtttcggt gatgacggtg aaaacctctg acacatgcag ctcccggaga    3840
cggtcacagc ttgtctgtaa gcggatgccg ggagcagaca gcccgtcag ggcgcgtcag     3900
cgggtgttgg cgggtgtcgg ggctggctta actatgcggc atcagagcag attgtactga    3960
gagtgcacca tatgcggtgt gaaataccgc acagatgcgt aaggagaaaa taccgcatca    4020
gattggctat                                                            4030
```